United States Patent
Ebanks et al.

(10) Patent No.: US 12,403,082 B2
(45) Date of Patent: Sep. 2, 2025

(54) COSMETIC COMPOSITIONS WITH IMPROVED WEAR AND TRANSFER RESISTANCE

(71) Applicant: L'ORÉal, Paris (FR)

(72) Inventors: Jody Ebanks, Clark, NJ (US); Komal Ladd, Kenilworth, NJ (US); Tsang-Min Huang, Scotch Plains, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/900,139

(22) Filed: Aug. 31, 2022

(65) Prior Publication Data
US 2023/0181449 A1 Jun. 15, 2023

(51) Int. Cl.
| | |
|---|---|
| A61K 8/81 | (2006.01) |
| A61K 8/46 | (2006.01) |
| A61K 8/55 | (2006.01) |
| A61K 8/67 | (2006.01) |

(52) U.S. Cl.
CPC ............ *A61K 8/8111* (2013.01); *A61K 8/466* (2013.01); *A61K 8/553* (2013.01); *A61K 8/67* (2013.01); *A61K 8/8152* (2013.01); *A61K 2800/42* (2013.01); *A61K 2800/522* (2013.01)

(58) Field of Classification Search
CPC ................................ A61K 8/8152; A61Q 1/04
See application file for complete search history.

(56) References Cited

U.S. PATENT DOCUMENTS

| | | | |
|---|---|---|---|
| 3,356,031 | A | 12/1967 | Glikin |
| 9,918,925 | B2 | 3/2018 | Debaud et al. |
| 10,071,046 | B2 | 9/2018 | Portal et al. |
| 10,258,552 | B2 | 4/2019 | Li et al. |
| 10,369,387 | B2 | 8/2019 | El-Khouri et al. |
| 10,617,625 | B2 | 4/2020 | Debeaud et al. |
| 10,675,226 | B2 | 6/2020 | El-Khouri |
| 10,744,074 | B2 | 8/2020 | El-Khouri |
| 10,772,806 | B2 | 9/2020 | El-Khouri |
| 10,780,040 | B2 | 9/2020 | El-Khouri |
| 10,894,010 | B2 | 1/2021 | El-Khouri et al. |
| 10,952,954 | B2 | 3/2021 | Rosario-Melendez et al. |
| 11,179,313 | B2 | 11/2021 | El-Khouri |
| 11,185,490 | B2 | 11/2021 | El-Khouri |
| 11,382,855 | B2 | 7/2022 | Bernard et al. |
| 11,464,731 | B2 | 10/2022 | El-Khouri et al. |
| 11,540,997 | B2 | 1/2023 | Farran et al. |
| 11,696,880 | B2 | 7/2023 | Farran et al. |
| 11,721,411 | B2 | 8/2023 | Xu et al. |
| 2006/0093568 | A1* | 5/2006 | Blin .................. A61Q 1/06 424/70.16 |
| 2009/0186055 | A1* | 7/2009 | Dumousseaux ......... A61Q 1/00 424/401 |
| 2018/0243202 | A1 | 8/2018 | El-Khouri |
| 2018/0263889 | A1 | 9/2018 | Ilekti et al. |
| 2018/0325800 | A1 | 11/2018 | Bernard et al. |
| 2019/0091130 | A1 | 3/2019 | Farran et al. |
| 2020/0276093 | A1 | 9/2020 | Farran et al. |
| 2020/0345613 | A1 | 11/2020 | Zhou et al. |
| 2021/0361557 | A1 | 11/2021 | Bernard et al. |
| 2021/0401723 | A1 | 12/2021 | Ebanks et al. |
| 2022/0202669 | A1 | 6/2022 | Saini et al. |
| 2022/0202691 | A1 | 6/2022 | Saini et al. |
| 2023/0036740 | A1 | 2/2023 | Farran et al. |

FOREIGN PATENT DOCUMENTS

| | | |
|---|---|---|
| FR | 1462829 A | 12/1966 |
| FR | 2871057 A1 | 12/2005 |
| WO | 2017173270 A1 | 10/2017 |
| WO | 2022129192 A1 | 6/2022 |

OTHER PUBLICATIONS

French Search Report, and Written Opinion, for corresponding French Application No. 2213037, dated Dec. 9, 2022.

* cited by examiner

*Primary Examiner* — Craig D Ricci
*Assistant Examiner* — Paul Hoerner
(74) *Attorney, Agent, or Firm* — MEAGHER EMANUEL LAKS GOLDBERG & LIAQ, LLP

(57) ABSTRACT

A cosmetic composition may be utilized to provide improved wear and transfer resistance. The cosmetic composition may include a (i) hydrogel dispersion in oil, the hydrogel having an ethylenic polymeric core, as well as (ii) a transfer-resistant film former, (iii) a hydrophilic active agent incorporated into the ethylenic polymeric core, or (iv) both (ii) and (iii). The dispersion may include a plurality of ethylenic polymeric core particles dispersed in a fatty substance that is liquid at 20° C. and 1 atmosphere that also includes a polymeric stabilizing agent.

19 Claims, No Drawings

COSMETIC COMPOSITIONS WITH IMPROVED WEAR AND TRANSFER RESISTANCE

CROSS-REFERENCE TO RELATED APPLICATIONS

The present application claims priority to FR 2113186 and U.S. 62/287,650, both filed on Dec. 9, 2021, both of which are incorporated by reference herein in their entirety.

TECHNICAL FIELD

The present disclosure is drawn to cosmetic composition, and in particular, cosmetic compositions having improved wear and transfer resistance.

BACKGROUND

Consumers expect that cosmetics used for extended periods of time, such as lipsticks, foundations and mascaras, will have excellent non-transfer properties against olive oil, acetic acid and saliva and keep consistent wear, such as no smudging or smearing. To achieve these properties, such compositions are often devoid of skin care ingredients (or contain very little) due to disruption of the film properties, which decrease the wear properties. It is a challenge to incorporate many skin-loving ingredients and actives into such formulas. Further, controlling the release of such skin-loving ingredients can be very difficult when they are incorporated into the products. These extended-wear products are also expected to provide certain aesthetic properties. For example, lipsticks are expected to be comfortable to wear and provide a shine, matte, or satin finish to the lips as desired. Finally, providing such features to an extended-wear product can be challenging if the product also requires providing volume.

BRIEF SUMMARY

To achieve these goals, a cosmetic composition may be provided. The cosmetic composition may be a cosmetic composition for use on lips. The cosmetic composition may include a hydrogel dispersion in oil. The dispersion may include an ethylenic polymeric core particle obtained by polymerization of monomers of: (a) ($C_1$-$C_4$) alkyl ($C_1$-$C_4$) (alkyl)acrylate in which the ($C_1$-$C_4$) alkyl group(s) are optionally substituted by one or more hydroxy groups and/or (di)($C_1$-$C_4$)(alkyl)amino groups; (b) poly[oxy ($C_1$-$C_4$) alkylene] ($C_1$-$C_4$) (alkyl)acrylate; and/or (c) ethylenic monomers comprising one or more groups selected from carboxy, anhydride, phosphoric acid, and sulfonic acid. The dispersion may include a polymeric stabilizing agent chosen from (d) ethylenic polymers of ($C_1$-$C_6$) (alkyl) acrylate of ($C_3$-$C_{12}$) cycloalkyl monomers; and/or (e) copolymers of ethylenic monomers of ($C_1$-$C_6$) ($C_3$-$C_{12}$) cycloalkyl (alkyl) acrylate and ($C_1$-$C_4$) alkyl ($C_1$-$C_4$) (alkyl)acrylate. The dispersion may include a fatty substance that is liquid at 20° C. and 1 atmosphere.

In some embodiments, the ethylenic polymers of ($C_1$-$C_6$) (alkyl) acrylate of ($C_3$-$C_{12}$) cycloalkyl monomers may be ethylenic homopolymers of ($C_1$-$C_6$) (alkyl) acrylate of ($C_3$-$C_{12}$) cycloalkyl. In some embodiments, the ethylenic polymers of ($C_1$-$C_6$) (alkyl) acrylate of ($C_3$-$C_{12}$) cycloalkyl monomers may be ethylenic homopolymers of ($C_3$-$C_{12}$) cycloalkyl(meth)acrylate. In some embodiments, the copolymers of ethylenic monomers of ($C_1$-$C_6$) ($C_3$-$C_{12}$) cycloalkyl ($C_1$-$C_4$) alkyl (alkyl)acrylate and ($C_1$-$C_4$) alkyl ($C_1$-$C_4$) (alkyl)acrylate may be copolymers of ($C_3$-$C_{12}$) cycloalkyl(meth)acrylate and ($C_1$-$C_4$) alkyl(meth)acrylate.

In some embodiments, the fatty substance is a volatile hydrocarbon. In some embodiments, the volatile hydrocarbon is isododecane.

In some embodiments, the dispersion may also include an additional particle. The additional particle may have a different chemical structure from the ethylenic polymeric core particle, the additional particle obtained by polymerization of monomers chosen from ethylenic monomers of (a), (b), and/or (c).

The cosmetic composition may include a transfer-resistant film former. In some embodiments, the transfer-resistant film former includes a silicone pullulan, a silicone norbornene, a pseudo block copolymer, a MQ resin, a T propyl siloxane resin, a MQT resin, or a combination thereof. In some embodiments, the film former includes a MQ resin, a polyester, a trimethylsiloxymethacrylate copolymer, or a dimethicone copolymer.

The cosmetic composition may include a hydrophilic active agent incorporated into the ethylenic polymeric core particle. In some embodiments, the hydrophilic active agent is a moisturizing agent, a desquamating agent, a humectant, an anti-aging agent, a healing agent, an antibacterial agent, a texture modifier, a colorant, a pigment modifying agent, a skin lightening agent, a vitamin, a swelling agent, or a combination thereof.

In some embodiments, the cosmetic composition may include other materials. In some embodiments, the cosmetic composition may include water, a colorant, an antioxidant, an ultraviolet (UV) filter, a mattifying agent, or a combination thereof.

In some embodiments, the cosmetic composition, external to the core particle, may include a hydrophilic active agent. In some embodiments, the hydrophilic active agent is a moisturizing agent, a desquamating agent, a humectant, an anti-aging agent, a mattifying agent, a healing agent, an antibacterial agent, a texture modifier, a colorant, a pigment modifying agent, a skin lightening agent, a vitamin, a swelling agent, or a combination thereof.

DETAILED DESCRIPTION

To overcome some or all of the issues with conventional techniques, a cosmetic composition may be provided that includes (i) a dispersion, and (ii) a transfer-resistant film former, a hydrophilic active agent incorporated into an ethylenic polymeric core particle of the dispersion, or both. It will be understood that transfer-resistance requires a transfer-resistant film former.

As used herein, the term "alkyl radical" refers to a linear or branched saturated C1-C8, in particular $C_1$-$C_6$, preferably C1-C4 hydrocarbon-based group such as methyl, ethyl, n-propyl, isopropyl, n-butyl, isobutyl and tert-butyl.

As used herein, the term "(C9-C22)alkyl" radical refers to a linear or branched, preferably linear, saturated C9-C22, in particular C10-C20, preferentially C12-C18, more preferentially C12-C16 hydrocarbon-based group, such as lauryl (C12), myristyl (C14), hexadecyl (C16), stearyl (C18), arachidyl (C20) or behenyl (C22); more particularly, (C9-C18)alkyl is a linear or branched, preferably linear, saturated C9-C18 hydrocarbon-based group.

As used herein, the term "alkylene" radical refers to a linear or branched divalent saturated C1-C8, in particular $C_1$-$C_6$, preferably $C_1$-$C_4$ hydrocarbon-based group such as methylene, ethylene or propylene.

As used herein, the term "(di) (C$_1$-C$_4$) (alkyl)amino" refers to an amino radical —NH2; a (C$_1$-C$_4$) alkylamino radical such as methylamino ethylamino; a di (C$_1$-C$_4$) alkylamino radical such as dimethylamino, diethylamino, preferably dimethylamino.

As used herein, the term "anhydrous" dispersion or composition means a dispersion or composition containing less than 2% by weight of water, or even less than 0.5% of water, and notably free of water; where appropriate, such small amounts of water may notably be provided by ingredients of the composition which may contain residual amounts thereof.

As used herein, the term "aryl" means a monocyclic or fused or non-fused polycyclic carbon-based group comprising from 6 to 22 carbon atoms, and in which at least one ring is aromatic. In some embodiments, the aryl radical refers to a monocyclic or fused or non-fused bicyclic, unsaturated cyclic aromatic radical comprising from 6 to 12 carbon atoms; preferably, the aryl group comprises 1 ring and contains 6 carbon atoms, such as phenyl. In some embodiments, the aryl radical is a phenyl, biphenyl, naphthyl, indenyl, anthracenyl or tetrahydronaphthyl.

As used herein, the term "aryloxy" radical refers to an aryl-oxy, i.e. aryl-O—, radical, with aryl as defined previously, preferably phenoxy.

As used herein, the term "aryl(C$_1$-C$_4$)alkoxy" radical refers to an aryl-(C$_1$-C$_4$)alkyl-O-radical, preferably benzoxy.

As used herein, the term "cyclic" radical refers to a cyclic saturated or unsaturated, aromatic or non-aromatic hydrocarbon-based group comprising from 1 to 3 rings, preferably 1 ring, and comprising from 3 to 10 carbon atoms, such as cyclohexyl or phenyl.

As used herein, the term "cycloalkyl" radical refers to a cyclic saturated hydrocarbon-based group comprising from 1 to 3 rings, preferably 2 rings, and comprising from 3 to 12 carbon atoms, preferably between 5 and 10 carbon atoms, such as cyclopentyl, cyclohexyl, cycloheptyl, norbornyl, or isobornyl, the cycloalkyl radical possibly being substituted with one or more (C$_1$-C$_4$)alkyl groups such as methyl; preferably, the cycloalkyl radical is an isobornyl group.

As used herein, the term "insoluble" monomer refers to any monomer of which the polymer, notably the homopolymer, is not in soluble form, i.e. not fully dissolved at a concentration of greater than 5% by weight at room temperature (20° C.) in said liquid hydrocarbon-based medium consisting of iii) liquid hydrocarbon-based fatty substances. However, the "insoluble" monomers may, as monomers, be soluble in the liquid hydrocarbon-based medium consisting of liquid hydrocarbon-based fatty substances iii) of the dispersion, it being understood that they become insoluble after polymerization.

As used herein, the term "soluble" monomer refers to any monomer of which the polymer, notably the homopolymer, is soluble, to 5% by weight, at 20° C. and at atmospheric pressure in the liquid hydrocarbon-based medium consisting of liquid hydrocarbon-based fatty substances iii) of the dispersion. The polymer, notably the homopolymer, is completely dissolved in the liquid carbon-based medium, visually at 20° C., i.e., no insoluble deposit or precipitate or agglomerate or sediment is visually noted.

As used herein, the term "ethylenic copolymer" means a polymer derived from the polymerization of different monomers, in particular at least two different monomers. Preferably, the ethylenic copolymer of the invention is derived from two or three different monomers, more preferentially derived from two different monomers.

As used herein, the term "ethylenic homopolymer" means a polymer derived from the polymerization of identical monomers.

As used herein, the term "ethylenic monomer" means an organic compound including one or more conjugated or non-conjugated unsaturations of >C=C< type, which is capable of polymerizing.

As used herein, the term "fatty substance" means an organic compound that is immiscible in water at ordinary room temperature (25° C.) and at atmospheric pressure (760 mmHg) (solubility of less than 5%, preferably 1% and even more preferentially 0.1%). They bear in their structure at least one hydrocarbon-based chain including at least 6 carbon atoms or a sequence of at least two siloxane groups. In addition, the fatty substances are generally soluble in organic solvents under the same temperature and pressure conditions, for instance ethanol, ether, liquid petroleum jelly or decamethylcyclopentasiloxane. These fatty substances are neither polyoxyethylenated nor polyglycerolated. They are different from fatty acids, since salified fatty acids constitute soaps that are generally soluble in aqueous media.

As used herein, the term "liquid" fatty substance notably refers to a fatty substance that is liquid at 25° C. and 1 atmosphere; preferably, said fatty substance has a viscosity of less than or equal to 7000 centipoises at 20° C.

As used herein, the term "hydrocarbon-based" fatty substance means a fatty substance which comprises at least 50% by weight, notably from 50% to 100% by weight, for example from 60% to 99% by weight, or even from 65% to 95% by weight, or even from 70% to 90% by weight, relative to the total weight of said fatty substance, of carbon-based compound, having a global solubility parameter in the Hansen solubility space of less than or equal to 20 (MPa)½, or a mixture of such compounds.

As used herein, the global solubility parameter δ according to the Hansen solubility space is defined in the article "Solubility parameter values" by Grulke in the book "Polymer Handbook", 3rd Edition, Chapter VII, pages 519-559, by the relationship δ=(dD2+dP2+dH2)½ in which: —dD characterizes the London dispersion forces arising from the formation of dipoles induced during molecular impacts, —dP characterizes the Debye interaction forces between permanent dipoles, —dH H characterizes the forces of specific interactions (such as hydrogen bonding, acid/base, donor/acceptor, etc.); The definition of solvents in the Hansen three-dimensional solubility space is described in the article by Hansen: The three-dimensional solubility parameters, J. Paint Technol. 39, 105 (1967).

As used herein, the term "oil" means a fatty substance that is liquid at room temperature (25° C.) and at atmospheric pressure.

As used herein, the term "hydrocarbon-based oil" means an oil formed essentially from, or even constituted of, carbon and hydrogen atoms, and optionally of oxygen and nitrogen atoms, and not containing any silicon or fluorine atoms. It may contain hydroxy, ester, ether, carboxylic acid, amine and/or amide groups.

As used herein, the term "volatile oil" means an oil (or non-aqueous medium) that can evaporate on contact with keratin materials, in particular the skin, in less than one hour, at room temperature and at atmospheric pressure. The volatile oil is a volatile cosmetic oil, which is liquid at room temperature, notably having a non-zero vapour pressure, at room temperature and at atmospheric pressure, in particular having a vapour pressure ranging from 0.13 Pa to 40 000 Pa (10' to 300 mmHg), preferably ranging from 1.3 Pa to 13,000 Pa (0.01 to 100 mmHg) and preferentially ranging from 1.3 Pa to 1300 Pa (0.01 to 10 mmHg).

As used herein, the term "non-volatile oil" means an oil with a vapour pressure of less than 0.13 Pa at room temperature and at atmospheric pressure.

As used herein, the term "silicone oil" means an oil comprising at least one silicon atom and notably at least one Si—O group. The silicone oil may be volatile or non-volatile.

As used herein, the term "dispersant" refers to a compound which can protect the dispersed particles from agglomerating or flocculating. This dispersant may be a surfactant, an oligomer, a polymer or a mixture of several thereof, bearing one or more functionalities with strong affinity for the surface of the ethylenic polymeric core particles to be dispersed; in particular, they can attach physically or chemically to the surface of the pigments. These dispersants also contain at least one functional group that is compatible with or soluble in the continuous medium. Said agent may be charged: it may be anionic, cationic, zwitterionic or neutral.

As used herein, the term "submicron" or "submicronic" refers to pigments having a particle size that has been micronized by a micronization method and having a mean particle size of less than a micrometer (μm), in particular between 0.1 and 0.9 μm, and preferably between 0.2 and 0.6 μm.

As used herein, the term "heteroaryl" means an optionally cationic, 5- to 22-membered, monocyclic or fused or non-fused polycyclic group, comprising from 1 to 6 heteroatoms chosen from nitrogen, oxygen, sulfur and selenium, at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridyl, imidazolyl, indolyl, isoquinolyl, naphthoimidazolyl, naphthoxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthyl and the ammonium salt thereof.

As used herein, the term "heterocyclic" means a 5- to 22-membered, monocyclic or fused or non-fused polycyclic aromatic or non-aromatic radical that may contain one or more unsaturations, including from 1 to 6 heteroatoms chosen from nitrogen, oxygen and sulfur.

As used herein, the term "heterocycloalkyl" means a saturated heterocyclic radical such as morpholinyl, piperazinyl or piperidyl.

As used herein, the term "organic or mineral acid salt" more particularly means salts chosen from a salt derived from a halogenated acid such as i) hydrochloric acid HCl, ii) hydrobromic acid HBr, iii) sulfuric acid H2SO4, iv) alkylsulfonic acids: Alk-S(O)2OH such as methylsulfonic acid and ethylsulfonic acid; v) arylsulfonic acids: Ar—S(O)2OH such as benzenesulfonic acid and toluenesulfonic acid; optionally hydroxylated carboxylic acids such as vi) citric acid; vii) succinic acid; viii) tartaric acid; ix) lactic acid; x) acetic acid CH3C(O)OH; xi) alkoxysulfinic acids: Alk-O—S(O)OH such as methoxysulfinic acid and ethoxysulfinic acid; xii) aryloxysulfinic acids such as tolueneoxysulfinic acid and phenoxysulfinic acid; xiii) phosphoric acid H3PO4; xiv) triflic acid CF3SO3H and xv) tetrafluoroboric acid HBF4; more preferentially, the organic or mineral acid salts are chosen from the salts of halogenated acids such as HCl and HBr, and of optionally hydroxylated carboxylic acids such as vi) citric acid; vii) succinic acid; viii) tartaric acid; ix) lactic acid; x) acetic acid CH3C(O)OH.

As used herein, the term "anionic counterion" means an anion or an anionic group derived from an organic or mineral acid salt which counterbalances the charge of the molecule in question; more particularly, the anionic counterion is chosen from: i) halides such as chloride or bromide; ii) nitrates; iii) sulfonates, including $C_1$-$C_6$ alkylsulfonates: Alk-S(O)2O— such as methylsulfonate or mesylate and ethylsulfonate; iv) arylsulfonates: Ar—S(O)2O—such as benzenesulfonate and toluenesulfonate or tosylate; v) citrate; vi) succinate; vii) tartrate; viii) lactate; ix) alkyl sulfates: Alk-O—S(O)O— such as methyl sulfate and ethyl sulfate; x) aryl sulfates: Alk-O—S(O)O— such as benzene sulfate and toluene sulfate; xi) alkoxy sulfates: Alk-O—S(O)2O— such as methoxy sulfate and ethoxy sulfate; xii) aryloxy sulfates: Ar—O—S(O)2O—, xiii) phosphates O═P(OH)2-O—, O═P(O—)2-OH, O═P(O—)3, HO—[P(O)(O—)]w-P(O)(O—)2 with w being an integer; xiv) acetate; xv) triflate; and xvi) borates such as tetrafluoroborate, xvii) disulfate (O═)2S(O—)2 or SO42- and monosulfate HSO4-; the anionic counterion, derived from an organic or mineral acid salt, ensures the electrical neutrality of the molecule; thus, it is understood that when the anion comprises several anionic charges, then the same anion can serve for the electrical neutrality of several cationic groups in the same molecule or else may serve for the electrical neutrality of several molecules; for example, a molecule which contains two cationic groups may contain either two "singly charged" anionic counterions or contain a "doubly charged" anionic counterion such as (O═)2S(O—)2 or O═P(O—)2-OH.

Moreover, the addition salts that may be used in the context of the present disclosure are notably chosen from addition salts with a cosmetically acceptable base such as the basifying agents as defined below, for instance alkali metal hydroxides such as sodium hydroxide, potassium hydroxide, aqueous ammonia, amines or alkanolamines.

For the purposes of the present disclosure, and unless otherwise indicated:

the "aryl" or "heteroaryl" radical or the aryl or heteroaryl part of a radical may be substituted with at least one substituent borne by a carbon atom, chosen from:
 a $C_1$-$C_6$ and preferably $C_1$-$C_4$ alkyl radical optionally substituted with one or more radicals chosen from hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;
halogen;
hydroxyl;
$C_1$-$C_2$ alkoxy;
$C_2$-$C_4$ (poly)hydroxyalkoxy;
amino;
an amino radical substituted with one or two identical or different $C_1$-$C_6$ alkyl radicals, optionally bearing at least one hydroxyl group;
acylamino (—NR—C(O)—R') in which the radical R is a hydrogen atom or a $C_1$-$C_4$ alkyl radical optionally bearing at least one hydroxyl group and the radical R' is a $C_1$-$C_2$ alkyl radical;

carbamoyl ((R)2N—C(O)—) in which the radicals R, which may be identical or different, represent a hydrogen atom or a $C_1$-$C_4$ alkyl radical optionally bearing at least one hydroxyl group;

alkylsulfonylamino (R'—S(O)2-N(R)—) in which the radical R represents a hydrogen atom or a $C_1$-$C_4$ alkyl radical optionally bearing at least one hydroxyl group and the radical R' represents a $C_1$-$C_4$ alkyl radical, or a phenyl radical;

an aminosulfonyl radical ((R)2N—S(O)2-) in which the radicals R, which may be identical or different, represent a hydrogen atom or a $C_1$-$C_4$ alkyl radical optionally bearing at least one hydroxyl group;

carboxylic in acid or salified (preferably with an alkali metal or a substituted or unsubstituted ammonium) form;

cyano;

nitro or nitroso;

polyhaloalkyl, preferentially trifluoromethyl;

the cyclic or heterocyclic part of a non-aromatic radical may be substituted with at least one substituent chosen from the following groups: a) hydroxyl; b) $C_1$-$C_4$ alkoxy, C2-C4 (poly)hydroxyalkoxy; c) $C_1$-$C_4$ alkyl;

alkylcarbonylamino (R—C(O)—N(R')—) in which the radical R' is a hydrogen atom or a $C_1$-$C_4$ alkyl radical optionally bearing at least one hydroxyl group, and the radical R is a C1-C2 alkyl radical or an amino radical optionally substituted with one or two $C_1$-$C_4$ alkyl groups, which may be identical or different, themselves optionally bearing at least one hydroxyl group, said alkyl radicals possibly forming, with the nitrogen atom to which they are attached, a saturated or unsaturated, optionally substituted 5- to 7-membered heterocycle optionally comprising at least one other nitrogen or non-nitrogen heteroatom;

alkylcarbonyloxy (R—C(O)—O—) in which the radical R is a $C_1$-$C_4$ alkyl radical or an amino group optionally substituted with one or two identical or different $C_1$-$C_4$ alkyl groups themselves optionally bearing at least one hydroxyl group, said alkyl radicals possibly forming with the nitrogen atom to which they are attached a saturated or unsaturated, optionally substituted 5- to 7-membered heterocycle, optionally comprising at least one other nitrogen or non-nitrogen heteroatom;

alkoxycarbonyl (R-G-C(O)—) in which the radical R is a $C_1$-$C_4$ alkoxy radical, G is an oxygen atom or an amino group optionally substituted with a $C_1$-$C_4$ alkyl group itself optionally bearing at least one hydroxyl group, said alkyl radical possibly forming with the nitrogen atom to which they are attached a saturated or unsaturated, optionally substituted 5- to 7-membered heterocycle, optionally comprising at least one other nitrogen or non-nitrogen heteroatom;

a cyclic or heterocyclic radical, or a non-aromatic part of an aryl or heteroaryl radical, may also be substituted with one or more oxo groups; and a hydrocarbon-based chain is unsaturated when it includes one or more double bonds and/or one or more triple bonds.

As used herein, the expression "at least one" is equivalent to "one or more". As used herein, the limits of a range of values are included in that range, notably in the expressions "between . . . and . . . " and "ranging from . . . to . . . ". As used herein, the expression "inclusive" for a range of concentrations means that the limits of the range are included in the defined interval.

As disclosed herein, a cosmetic composition may be provided that includes (i) a dispersion, and (ii) a transfer-resistant film former, a hydrophilic active agent incorporated into an ethylenic polymeric core particle of the dispersion, or both.

Dispersion.

The dispersion can be understood as a hydrogel-in-oil dispersion. There are three components of the dispersion: (a) an ethylenic polymeric core particle, (b) a fatty substance that is liquid at 20° C. and 1 atmosphere, and (c) a polymeric stabilizing agent ("stabilizers").

In some embodiments, the dispersion may be present from at least about 5 wt. % based on the total weight of the cosmetic composition.

The dispersion, combined with a wide range of film formers, can surprisingly improve transfer resistance while maintaining wear resistance. Further, the dispersion is a Pickering dispersion and the core particles form a hydrogel. By incorporating hydrophilic materials into the hydrogel, the hydrogel swells, which provides volume.

Polymer Particles

To obtain the dispersion, one can polymerize particular monomers that are capable of forming the polymer "core" in the presence of a polymeric statistical stabilizer comprising in minor amount a part that is soluble and in major amount a part that is insoluble in the dispersion medium, i.e., in the liquid hydrocarbon-based fatty substance(s).

In some embodiments, the cosmetic composition includes a plurality of ethylenic polymeric core particles. In some embodiments, each ethylenic polymeric core particle has a single composition. In some embodiments, the plurality of ethylenic polymeric core particles includes at least two particles with different compositions.

In some embodiments, the ethylenic polymeric core particles of the dispersion may be made of ethylenic monomers of:

$a_1$) ($C_1$-$C_4$)alkyl ($C_1$-$C_4$)(alkyl)acrylate in which the ($C_1$-$C_4$) alkyl group(s) are optionally substituted by one or more group (s) chosen from hydroxy, and (di) ($C_1$-$C_4$)(alkyl)amino; and/or $a_2$) poly[oxy($C_1$-$C_4$)alkylene] ($C_1$-$C_4$)(alkyl)acrylate, and $a_3$) ethylenic monomers comprising one or more carboxy, anhydride, phosphoric acid, sulfonic acid groups.

According to another particular embodiment of the instant disclosure, the ethylenic polymeric core particle of the dispersion may be made up of several polymer (s) chosen from among $b_1$) at least one copolymer of ethylenic monomers of:

$a_1$) ($C_1$-$C_4$)alkyl ($C_1$-$C_4$)(alkyl)acrylate in which the ($C_1$-$C_4$) alkyl group (s) are optionally substituted by one or more group (s) chosen from hydroxy, and (di) ($C_1$-$C_4$)(alkyl)amino; and/or $a_2$) poly[oxy($C_1$-$C_4$)alkylene] ($C_1$-$C_4$)(alkyl)acrylate, and $a_3$) ethylenic monomers comprising one or more carboxy, anhydride, phosphoric acid, sulfonic acid groups; and $b_2$) at least one polymer of ethylenic monomers comprising one or more carboxy, anhydride, phosphoric acid or sulfonic acid groups.

Preferably, the ethylenic monomers comprising one or more carboxy, anhydride, phosphoric acid, sulfonic acid $a_3$) groups are chosen from ethylenic monomers comprising one or more carboxy groups, more preferably ($C_1$-$C_4$) (alkyl) acrylic acids such as (meth)acrylic acid, in particular acrylic acid. Preferably, the ethylenic monomers of ($C_1$-$C_4$)alkyl ($C_1$-$C_4$)(alkyl)acrylate in which ($C_1$-$C_4$) alkyl denote (meth)

acrylate of (C₁-C₄) alkyl such as ethyl(meth)acrylate or (methyl meth)acrylate, in particular methyl acrylate and ethyl acrylate.

Preferably, the ethylenic monomers of (C₁-C₄)alkyl (C₁-C₄)(alkyl)acrylate in which the (C₁-C₄) alkyl group or groups are substituted by one or more groups chosen from hydroxy, (di) ((C₁-C₄) alkyl)amino are chosen from ethylenic monomers of (C₁-C₄) (C₁-C₄) alkyl (alkyl) acrylate substituted with a hydroxy group or with a (di) ((C₁-C₄) group)alkyl)amino. According to one embodiment, the ethylenic monomers of (C₁-C₄) (C₁-C₄) alkyl (alkyl) acrylate in which the (C₁-C₄) alkyl group (s) are substituted by one or more hydroxy groups, are substituted by a hydroxy group such as 2-hydroxyethyl(meth)acrylate, in particular 2-hydroxyethyl acrylate (HEA).

According to another embodiment, the ethylenic monomers of (C₁-C₄)alkyl (C₁-C₄)(alkyl)acrylate in which the (C₁-C₄) alkyl group (s) are optionally substituted by one or more group (s) chosen from hydroxy, and (di) (C₁-C₄) (alkyl)amino, are substituted by a di (C₁-C₄) alkyl) amino group such as a dimethylamino group such as 3-(dimethylamino) propyl(meth)acrylate, 2-(dimethylamino)ethyl (meth)acrylate.

According to a particular embodiment of the instant disclosure, the ethylenic polymeric core particles of the dispersion contain particles A1 consisting of copolymers of ethylenic monomers:
a₁) (C₁-C₄)alkyl (C₁-C₄)(alkyl)acrylate in which the (C₁-C₄) alkyl group (s) are optionally substituted by one or more group (s) chosen from hydroxy, and (di) (C₁-C₄) (alkyl)amino; and/or
a₂) poly[oxy(C₁-C₄)alkylene] (C₁-C₄)(alkyl)acrylate, and
a₃) ethylenic monomers comprising one or more carboxy, anhydride, phosphoric acid, sulfonic acid,
preferably consisting of copolymers of ethylenic monomers a1) and a3), or a2) and a3), more preferably a1) and a3).

According to a particular embodiment of the instant disclosure, the ethylenic polymeric core particles of the dispersion may contain particles A'1 consisting of copolymers of ethylenic monomers a'1) (C₁-C₄)alkyl (C₁-C₄)(alkyl)acrylate and a3) ethylenic monomers comprising one or more carboxy, anhydride, phosphoric acid, sulfonic acid.

According to another particular embodiment of the instant disclosure, the ethylenic polymeric core particles of the dispersion may contain particles A'2 consisting of copolymers of ethylenic monomers a"1) (C₁-C₄) (alkyl) (C₁-C₄) alkyl acrylate substituted with one or more groups chosen from hydroxy, (di) ((C₁-C₄) alkyl) amino, preferably substituted with a hydroxy group such as 2-hydroxyethylacrylate (HEA) and a3) monomers ethylenic comprising one or more carboxy, anhydride, phosphoric acid, sulfonic acid.

According to a preferred embodiment, the ethylenic polymeric core particles of the dispersion may contain particles A'1 and particles A'2 as described above and more preferably the ethylenic polymeric core particles of the dispersion are a mixture of particles A'1 and A'2, in particular in a mass ratio (mass of particles A'1/mass of particles A'2) of between 0.3 and 3, more particularly between 0.5 and 2.8, even more preferably between 0.6 and 2.

According to another particular embodiment of the instant disclosure the ethylenic polymeric core particles of the dispersion may be made up of a mixture of b1) at least one copolymer of ethylenic monomers of a1) and/or a2) and a3) as described above and b2) at least one polymer of ethylenic monomers comprising one or more carboxy, anhydride, phosphoric acid or sulfonic acid groups.

According to another particular embodiment of the instant disclosure the ethylenic polymeric core particles of the dispersion may be made up of a mixture of b1) at least one copolymer of ethylenic monomers of a1) and a3) as described above and b2) at least one polymer of ethylenic monomers comprising one or more carboxy, anhydride, phosphoric acid or sulfonic acid groups.

According to a particular form of the instant disclosure, b2) denotes a homopolymer of ethylenic monomers comprising one or more carboxy, or anhydride, or phosphoric acid or sulfonic acid groups, preferably comprising a carboxy group, more preferably acid (meth)acrylic and even more preferably acrylic acid.

The ethylenic polymeric core particles can be crosslinked or uncrosslinked.

According to one embodiment of the instant disclosure, the ethylenic polymeric core particles contain ethylenic copolymers A'1 resulting from the polymerization of monomer of formula (I) with ethylenic monomers comprising one or more carboxy, anhydride, phosphoric acid, sulfonic acid a₃ groups.

$$H_2C=C(R)-C(O)-O-R' \quad (I)$$

in which formula (I): R represents a hydrogen atom or a (C₁-C₄)alkyl group such as methyl, and R' represents a (C₁-C₄)alkyl group such as methyl or ethyl, preferably a C₁-C₄ alkyl acrylate such as methyl acrylate.

According to a particular embodiment of the instant disclosure the (C₁-C₄) (C₁-C₄) (alkyl) acrylate monomers denote the C₁-C₄ alkyl(meth)acrylate monomers preferably chosen from methyl(meth)acrylate, ethyl(meth)acrylate, n-propyl(meth)acrylate, isopropyl(meth)acrylate, n-butyl (meth)acrylate, (meth)acrylate isobutyl, tert-butyl(meth) acrylate and more preferably chosen from methyl(meth) acrylate, ethyl(meth)acrylate and even more preferably chosen from methyl acrylate and ethyl acrylate.

According to an advantageous embodiment of the instant disclosure, the dispersion may include from 60% to 99% by weight, in particular from 70% to 99% by weight, preferably from 80% to 95% by weight, in particular from 85% to 93% by weight of monomers constituting the ethylenic polymeric core particles relative to the total weight of polymers contained in said dispersion.

Preferably, the monomers capable of forming the ethylenic polymeric core particles are chosen from monomers which are insoluble in the hydrocarbon-based liquid fatty substance (s) of the dispersion.

In some embodiments, the insoluble monomers may preferably represent from 80 to 100% by weight, more preferably from 90 to 100% by weight, even more preferably from 95% to 100% by weight and even more particularly 100% by weight, of the total weight of monomers forming the ethylenic polymeric core particles.

Ethylenic Monomers Bearing an Acid, Anhydride or Aryl Function:

The ethylenic polymeric core particles may comprise ethylenic polymers that comprise or consist of ethylenic monomers a₃) comprising one or more carboxy, anhydride, phosphoric acid or sulfonic acid groups.

More particularly the ethylenic monomers a₃) may comprise one or more carboxy, anhydride, phosphoric acid or sulfonic acid groups are chosen from (1), (2), (3) and (4):
(1) R¹(R²)C=C(R3)-Acid with R¹, R² and R³ representing a hydrogen atom or a CO₂H, H₂PO₄ or SO₃H group, and Acid representing a carboxyl, phosphoric acid or sulfonic acid group, preferably carboxyl, and also the organic or mineral base salts thereof such as the alkali metal or alkaline-earth metal salts, such as C(O)ONa or C(O)OK, preferably (1) represents (5) H2C=C(R)—C(O)—O—H with R representing a hydrogen atom or a ($C_1$-$C_4$)alkyl group such as methyl, and also the organic or mineral base salts thereof such as the alkali metal or alkaline-earth metal salts, such as Na or K;

(2) $H_2C$=C(R)—C(O)—N(R')-Alk-Acid with R and R', which may be identical or different, representing a hydrogen atom or a ($C_1$-$C_4$)alkyl group; Alk represents a ($C_1$-$C_6$)alkylene group optionally substituted with at least one group chosen from Acid as defined previously and hydroxyl; and Acid is as defined previously, preferably carboxyl, phosphoric, or sulfonic acid, and also the organic or mineral base salts thereof such as the alkali metal or alkaline-earth metal salts such as C(O)ONa or C(O)OK;

(3) Ar—($R^a$)C=C($R^b$)—$R^c$ with $R^a$, $R^b$ and $R^c$, which may be identical or different, representing a hydrogen atom or a ($C_1$-$C_4$)alkyl group, and Ar representing an aryl group, preferably benzyl, optionally substituted with at least one acid group $CO_2H$, $H_2PO_4$ or $SO_3H$, preferably substituted with a $CO_2H$ or $SO_3H$ group, and also the organic or mineral base salts thereof such as the alkali metal or alkaline-earth metal salts such as C(O)ONa or C(O)OK;

(4) maleic anhydride of formulae (4a) and (4b):

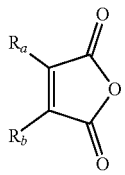

(4a)

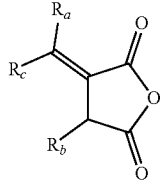

(4b)

in which formulae (4b) and (4b) $R_a$, $R_b$ and $R_c$, which may be identical or different, represent a hydrogen atom or a ($C_1$-$C_4$)alkyl group; preferably, $R_a$, $R_b$ and $R_c$ represent a hydrogen atom. Preferentially, the ethylenically unsaturated anhydride monomer is of formula (4b) and more preferentially is maleic anhydride.

More particularly, in some embodiments, the ethylenic monomer $a_3$) comprising one or more carboxy, anhydride, phosphoric acid or sulfonic acid groups is chosen from (1) and (4), in particular (5) and more particularly (5) and even more preferably acrylic acid.

According to another particular embodiment of the instant disclosure, the polymer constituting the ethylenic polymeric core particles and notably A'1 and/or b1) is an ethylenic acrylate copolymer derived from the polymerization:

at least one monomer a1) of formula (I) as defined previously, preferably a $C_1$-$C_4$ alkyl acrylate such as methyl acrylate or ethyl acrylate; and at least one monomer a3) of formula (5) and also the organic or mineral base salts thereof such as the alkali metal or alkaline-earth metal salts such as Na or K:

In some embodiments, the amount of acrylic acid ranges from 0.01% to 30% by weight relative to the total weight of copolymer A'1 or b1, preferably between 0.1% and 20% by weight relative to the weight of the polymer(s) of the ethylenic core particles. More particularly A'1 or b1), is in particular a copolymer resulting from the copolymerization of acrylic acid with one or more $C_1$-$C_4$ alkyl(meth)acrylate monomers, in particular chosen from methyl(meth)acrylate, and ethyl(meth)acrylate.

According to another embodiment, the polymer constituting the ethylenic polymeric core particles and notably A'1) and/or b1) is an ethylenic acrylate copolymer derived from the polymerization:

of at least two different monomers $a_1$): of formula (I) as defined previously, preferably a $C_1$-$C_4$ alkyl(meth)acrylate such as methyl(meth)acrylate or ethyl(meth)acrylate; and of a monomer $a_3$) of formula (5) as defined previously, as well as its salts of organic or inorganic bases such as alkalis or alkaline-earth metals such as Na or K, preferably acrylic acid. Even more preferably A'1 and/or b1) results from the polymerization of methyl acrylate, ethyl acrylate and acrylic acid. According to one embodiment, the ethylenic monomer $a_3$) comprising one or more carboxy, anhydride, phosphoric acid, sulfonic acid groups is chosen from crotonic acid, maleic anhydride, itaconic acid, fumaric acid, maleic acid, styrenesulfonic acid, vinylbenzoic acid, vinylphosphoric acid, acrylic acid, methacrylic acid, acrylamidopropanesulfonic acid, acrylamidoglycolic acid, and their salts, even more preferably the monomer ethylenic comprising one or more carboxy, anhydride, phosphoric acid, sulfonic acid represents acrylic acid and its salts.

According to one embodiment, the dispersion includes at least one type of particle. In some embodiments, the dispersion includes at least two types of different particles. In some embodiments, the dispersion includes 2 to 5 types of particles. In some embodiments, the dispersion includes two types of different particles.

In some embodiments, the dispersion comprises at least 2 types of different core particles, preferably two types of core particles which are copolymers of different chemical structure derived from monomers $a_1$) and/or $a_2$) and $a_3$), in particular which are copolymers of different chemical structure obtained by polymerization of monomers $a_1$) and $a_3$).

In some embodiments, the different core particles preferably comprise ethylenic copolymers (IA) of:
a"1) ($C_1$-$C_4$)alkyl ($C_1$-$C_4$)(alkyl)acrylate in which the ($C_1$-$C_4$) alkyl group (s) are optionally substituted by one or more group (s) chosen from hydroxy, and (di) ($C_1$-$C_4$) (alkyl)amino, preferably hydroxy and/or
$a_2$) oly[oxy($C_1$-$C_4$)alkylene] ($C_1$-$C_4$)(alkyl)acrylate, and
$a_3$) ethylenic monomers comprising one or more carboxy, anhydride, phosphoric acid, sulfonic acid, preferably carboxy groups; preferably ethylenic copolymers of $a'_1$) and $a_3$).

More particularly the ethylenic monomers $a_3$) comprising one or more carboxy, anhydride, phosphoric acid, sulfonic acid groups are chosen from (1), (2), (3), and (4) as defined above and denote in particular (5) as well as its salts of organic or inorganic bases such as alkalis or alkaline earth metals such as Na or K.

In some embodiments, the different core particles preferably comprise i) ethylenic copolymers (I'A) resulting from the polymerization of:

a'''$_1$ of at least one monomer of formula (I') H$_2$C=C(R)—C(O)—O—R", in which R represents a hydrogen atom or a (C$_1$-C$_4$)alkyl group such as methyl, and R" represents a (C$_1$-C$_4$)alkyl group substituted with one or more hydroxyl groups (preferably, the alkyl group is substituted at the end of the chain with a hydroxyl group), such as hydroxymethyl or 2-hydroxyethyl; preferably, (I') represents a C$_1$-C$_4$ hydroxyalkyl(meth)acrylate such as hydroxyethyl acrylate; and a$_3$") of at least one monomer of formula (5) as defined previously, as well as its salts of organic or inorganic bases such as alkalis or alkaline-earth metals such as Na or K.

According to yet another particular embodiment, the different particle(s) preferably comprise an ethylenic copolymer (IB) resulting from the polymerization of:

a2") of at least one monomer of formula (I') H$_2$C=C(R)—C(O)—O-[ALK-O]$_p$—R', in which R represents a hydrogen atom or a (C$_1$-C$_4$)alkyl group such as methyl, R' represents a (C$_1$-C$_4$)alkyl group such as methyl or ethyl, preferably a C$_1$-C$_4$ alkyl acrylate such as methyl acrylate; ALK represents a (C$_1$-C$_6$)alkylene group optionally substituted with at least one group chosen from Acid as defined previously and hydroxyl; preferably, ALK represents a (C$_1$-C$_4$)alkylene group such as ethylene, propylene, butylene or isobutylene; more preferentially, ALK represents an ethylene group; and p represents an integer greater than or equal to 1 and less than or equal to 100; and a3") of at least one monomer of formula (5) as defined previously, as well as its salts of organic or inorganic bases such as alkalis or alkaline-earth metals such as Na or K, preferably acrylic acid.

In some embodiments, the core particles may include more than 50% of one monomer, and less than 50% of another monomer. For example, the core particles may include more than 75% 2-hydroxyethyl acrylate and less than 25% acrylic acid.

In some embodiments, one or more of the monomers is less than 100% neutralized.

According to this embodiment, the different particle(s) may preferably comprise ethylenic copolymers (IC) obtained from the polymerization of:

a'''$_1$) (C$_1$-C$_4$) (alkyl) acrylate (C$_1$-C$_4$) alkyl monomers, preferably of formula (I) defined above; and/or a$_2$) poly[oxy(C$_1$-C$_4$)alkylene] (C$_1$-C$_4$)(alkyl)acrylate, and a$_3$) ethylenic monomers comprising one or more carboxy, anhydride, phosphoric acid, sulfonic acid groups, preferably chosen from (1), (2), (3), and (4) as defined above, more particularly of formula (5)) as well as its salts of organic or inorganic bases such as alkalis or alkaline-earth metals such as Na or K and even more preferably acrylic acid, preferably ethylenic copolymers (IC) resulting from the polymerization of monomers a'''$_1$) and a$_3$), the monomers a'''$_1$) preferably denoting C$_1$-C$_4$ alkyl (meth) acrylates, in particular ethyl (meth) acrylate, methyl (meth) acrylate more preferably methyl acrylate, ethyl acrylate.

More preferably, the copolymers (IC) result from the polymerization of several different monomers a'''$_1$) and of monomers a$_3$), even more preferably from ethyl(meth)acrylate with methyl(meth)acrylate and monomers a$_3$), more particularly methyl acrylate with ethyl acrylate and monomers a$_3$).

According to another embodiment, the dispersion comprises at least 2 types of different particles, preferably 2 types of different particles which are chosen from copolymers obtained by polymerization of monomers a$_1$) and a$_3$) as defined. previously, and b$_2$) polymers of ethylenic monomers comprising one or more carboxy, anhydride, phosphoric acid, sulfonic acid, preferably carboxy groups.

According to this embodiment, the copolymers are preferably chosen from copolymers (IC) as described above.

The polymers of ethylenic monomers b$_2$) preferably denote the homopolymer (ID), more preferably a homopolymer of monomers chosen from (1), (2), (3), and (4) as defined above, more particularly of monomers of formula (5) as well as its salts of organic or inorganic bases such as alkalis or alkaline-earth metals such as Na or K and even more preferably of acrylic acid.

The ethylenic polymeric core particle(s) of the dispersion (have) preferably a number-average size is greater than 50 nm.

The final size of the core particles of structure (ID) included in the dispersion may preferably be greater than 50 nm. In particular, a number-average size ranging from 50 nm to 600 nm; more particularly ranging from 100 nm to 500 nm, even more particularly ranging from 150 nm to 400 nm.

The final size of the core particles of structure (IA), (IB), (IC) or (IE) included in dispersion (A) is preferably greater than 100 nm. In particular, a number-average size ranging from 100 nm to 100 μm; more particularly ranging from 500 nm to 10 μm.

The mean size of the ethylenic polymeric core particles is determined via conventional methods known to those skilled in the art. A Malvern brand NanoZS model laser particle size analyser (which is particularly suitable for submicron dispersions) makes it possible to measure the size distribution of these samples. The operating principle of this type of machine is based on dynamic light scattering (DLS), also known as quasi-elastic light scattering (QELS) or photon correlation spectroscopy (PCS). It is also possible to determine the particle size by transmission microscopy.

The sample is pipetted into a disposable plastic tank (four transparent faces, side length of 1 cm and volume of 4 mL) placed in the measuring cell. The data are analysed on the basis of a cumulant fit method which leads to a monomodal particle size distribution characterized by an intensity-weighted mean diameter d (nm) and a size polydispersity factor Q. The results may also be expressed in the form of statistical data such as D10; D50 (median), D90 and the mode.

Other particle size techniques make it possible to obtain this type of information, such as analysis of the individual tracking of particles (Nanoparticle Tracking Analysis, NTA), laser scattering (LS), acoustic extinction spectroscopy (AES) spatial-filter Doppler velocimetry or image analysis.

Preferably, the monomers that are capable of forming the ethylenic core of the particle are chosen from monomers that are insoluble in the liquid hydrocarbon-based medium consisting of liquid hydrocarbon-based fatty substances. The insoluble monomers notably represent 100% by weight relative to the total weight of the monomers forming the polymeric core of the particle.

Preferably, the constituent monomers of the ethylenic core particles are chosen from monomers insoluble in the liquid hydrocarbon-based medium consisting of liquid fatty substance(s) hydrocarbon(s). The insoluble monomers represent in particular 80% to 100% by weight, preferably 90% to 100% by weight, more preferably 95% to 100% by weight, even more preferably 100% by weight, of the total weight of the monomers forming the ethylenic core particles particles(s).

The Stabilizer(s)

The dispersion also includes one or more polymeric stabilizing agents ("stabilizers"). Preferably, only one type of stabilizer is used in the composition.

According to another particular embodiment, the stabilizer(s) are chosen from d) ethylenic homopolymers of ($C_3$-$C_{12}$)cycloalkyl ($C_1$-$C_6$)(alkyl)acrylate monomers, preferably ($C_3$-$C_{12}$)cycloalkyl(meth)acrylate ethylenic homopolymers; more particularly ethylenic homopolymers derived from the polymerization of monomers of formula: $H_2C=C(R)-C(O)-O-R''$ with R as defined previously, and R'' representing a ($C_5$-$C_{10}$)cycloalkyl group such as norbornyl or isobornyl, preferably isobornyl.

More particularly, the stabilizer(s) may consist of ethylenic polymers chosen from ethylenic homopolymers d) or d') derived from the polymerization of monomers having the following formula: $H_2C=C(R)-C(O)-O-R'''$, where R represents a hydrogen atom or a ($C_1$-$C_4$)alkyl group such as methyl, and R''' representing a ($C_5$-$C_{10}$)cycloalkyl group such as norbornyl or isobornyl, preferably isobornyl.

According to a particular embodiment, the stabilizer(s) may be chosen from e) copolymers of ethylenic monomers of $e_1$) ($C_3$-$C_{12}$)cycloalkyl ($C_1$-$C_6$)(alkyl)acrylate, and of $e_2$) ($C_1$-$C_4$)alkyl ($C_1$-$C_4$)(alkyl)acrylate, preferably copolymers of ($C_3$-$C_{12}$)cycloalkyl(meth)acrylate and of ($C_1$-$C_4$)alkyl (meth)acrylate.

According to another embodiment, the stabilizer(s) may be chosen from e') ethylenic copolymers of $e_1$) ($C_3$-$C_{12}$) cycloalkyl ($C_1$-$C_6$)(alkyl)acrylate, and of $e_2$) ($C_1$-$C_4$)alkyl ($C_1$-$C_4$)(alkyl)acrylate, preferably copolymers e1) of ($C_3$-$C_{12}$)cycloalkyl(meth)acrylate and $e_2$) of ($C_1$-$C_4$)alkyl(meth)acrylate.

More particularly, the stabilizer(s) ii) are chosen from the ethylenic copolymers e) of monomers of formula (IV) and of monomers of formula (III):

$H_2C=C(R)-C(O)-O-R'$     (III)

$H_2C=C(R)-C(O)-O-R''$     (IV)

in which R, which may be identical or different, represents a hydrogen atom or a ($C_1$-$C_4$)alkyl group such as methyl; R', which may be identical or different, represents a ($C_1$-$C_4$) alkyl group such as methyl or ethyl; and R'' represents a ($C_5$-$C_{10}$)cycloalkyl group such as norbornyl or isobornyl, preferably isobornyl.

According to another particular embodiment of the instant disclosure, R'' represents a ($C_5$-$C_{10}$)cycloalkyl group such as norbornyl or isobornyl, preferably isobornyl.

According to a particular embodiment, the stabilizer(s) may consist of ethylenic copolymers e) chosen from $e_1$) polymers of ($C_3$-$C_{12}$)cycloalkyl ($C_1$-$C_6$)(alkyl)acrylate monomers notably of formula (IV) and of formula (III) as defined previously.

More particularly, the stabilizer(s) may consist of ethylenic copolymers e) chosen from $e'_1$) norbornyl(meth)acrylate or isobornyl (meth)acrylate, preferably isobornyl (meth) acrylate, and $e'_2$) methyl(meth)acrylate or ethyl(meth) acrylate.

According to another embodiment, the stabilizer(s) may be chosen from the ethylenic copolymers e) derived from the polymerization $e_1$) of a monomer of formula (IV) as defined previously and $e_2$) of two different monomers of formula (III) as defined previously.

Preferentially, the stabilizer(s) ii) are chosen from copolymers derived from the polymerization of $e_1$) one monomer of formula (IV) as defined previously notably chosen from isobornyl (meth)acrylate and $e_2$) of two different monomers of formula (III) as defined previously, notably different $C_1$-$C_4$ alkyl(meth)acrylates, preferably methyl and ethyl acrylate.

Particularly, the stabilizer may be chosen from d) homopolymers of (C3 C12)cycloalkyl ($C_1$-$C_6$)(alkyl)acrylate monomers; and e) statistical copolymers of $e_1$) (C3 C12)cycloalkyl ($C_1$-$C_6$)(alkyl)acrylate and $e_2$) ($C_1$-$C_4$)alkyl ($C_1$-$C_4$)(alkyl)acrylate with a weight ratio $e_1/e_2$ of greater than 4. Advantageously, said weight ratio ranges from 4.5 to 19. More advantageously, said weight ratio $e_1/e_2$ ranges from 5 to 15 and more preferentially said weight ratio ranges from 5.5 to 12.

More particularly, the stabilizer may be a polymer chosen from d') isobornyl (meth)acrylate homopolymer and e) statistical copolymers of $e_1'$) isobornyl (meth)acrylate and of $e_2'$) $C_1$-$C_4$ alkyl(meth)acrylate preferably present in an isobornyl (meth)acrylate/$C_1$-$C_4$ alkyl(meth)acrylate weight ratio ($e_1/e_2$) of greater than 4. Advantageously, said weight ratio $e_1'/e_2'$ ranges from 4.5 to 19. Advantageously, said weight ratio e1'/e2' ranges from 5 to 15 and more preferentially said weight ratio $e_1'/e_2'$ ranges from 5.5 to 14.

The stabilizing agent(s) as disclosed herein preferably comprise 80% to 100% by weight of monomer soluble in liquid hydrocarbon fatty substances iii), in particular from 85% to 95% by weight of soluble monomer, alone or as a mixture, relative to the total weight of monomers of the stabilizing agent (s). The stabilizer (co)polymer(s) may comprise particularly between 0% and 20% by weight, in particular between 5% and 15% by weight of monomer insoluble in liquid hydrocarbon fatty substances of the dispersion, alone or as a mixture relative to the total weight of monomers of the stabilizing agent(s).

Preferably, the stabilizer(s) and the particle(s) have a number-average molecular weight (Mn) of between 1000 and 1,000,000 g/mol, notably between 5000 and 500,000 g/mol and better still between 10,000 and 300,000 g/mol.

According to a particular embodiment, the dispersion may include from 5% to 40% by weight, in particular from 7% to 20% by weight, notably from 8% to 15% by weight and preferably from 9% to 13% by weight of ($C_3$-$C_{12}$)cycloalkyl (C1 C6)(alkyl)acrylate monomers d) or e1), relative to the total weight of polymers contained in said dispersion.

The stabilizer(s) may be present in the dispersion in an amount of between 0.01% and 30% by weight relative to the total weight of the dispersion, more particularly between 0.1% and 20% by weight, preferably between 0.5% and 10% by weight, more preferentially between 0.7% and 4.5% by weight relative to the total weight of the dispersion.

In some embodiments, the amount of stabilizer(s) may be between 0.05% and 30% by weight relative to the total weight of the dispersion without water, preferably between 0.2% and 20% by weight, notably between 2% and 15% by weight, more particularly between 2% and 10% by weight, more preferentially between 2.5% and 5% by weight relative to the total weight of the dispersion where the dispersion includes water.

In some embodiments, the amount of stabilizer(s) may be between 0.01% and 20% by weight relative to the total weight of said dispersion with water, preferably between 0.1% and 15% by weight, notably between 0.9% and 10% by weight, more particularly between 1% and 5% by weight, more preferentially between 2 and 3.5% by weight relative to the total weight of the dispersion where the dispersion includes water.

In some embodiments, the amount of stabilizer(s) may be are present in an amount of between 5% and 40% by weight relative to the total weight of the ethylenic core particles+ stabilizer(s), more particularly between 8% and 30% by weight, preferably between 9.8% and 12.5% by weight relative to the total weight of the ethylenic core particles+ stabilizer(s).

The Hydrocarbon-Based Liquid Fatty Substance(s)

The dispersion of polymer particles according to the instant disclosure also includes one or more hydrocarbon-based liquid fatty substances in which said particles are dispersed.

In some embodiments, the hydrocarbon-based liquid fatty substance(s) are chosen from hydrocarbons, in particular alkanes, oils of animal origin, oils of plant origin, glycerides or fluorinated oils of synthetic origin, fatty alcohols, esters of fatty acids and/or of fatty alcohols, non-silicone waxes, and silicones; in particular, the liquid hydrocarbon-based fatty substance(s) are hydrocarbon-based oils, which are preferably volatile, or are a mixture of different volatile oils, more particularly isododecane.

The hydrocarbon-based liquid fatty substances are notably chosen from $C_6$-$C_{16}$ hydrocarbons or hydrocarbons comprising more than 16 carbon atoms and up to 50 carbon atoms, preferably between $C_6$ and $C_{16}$, and in particular alkanes, oils of animal origin, oils of plant origin, glycerides, fatty alcohols, fatty acid and/or fatty alcohol esters, and silicones.

In some embodiments, the fatty alcohols, fatty esters and fatty acids more particularly contain one or more linear or branched, saturated or unsaturated hydrocarbon-based groups comprising 6 to 50 carbon atoms, which are optionally substituted, in particular, with one or more (in particular 1 to 4) hydroxyl groups. If they are unsaturated, these compounds may comprise one to three conjugated or unconjugated carbon-carbon double bonds.

As regards the $C_6$-$C_{16}$ alkanes, they may be linear or branched, and possibly cyclic. Examples that may be mentioned include hexane, decane, undecane, dodecane, tridecane or isoparaffins, such as isohexadecane, isodecane or isododecane, and their mixtures such as the combination of undecane and tridecane such as for example CETIOL UT®, or mixtures of $C_9$-$C_{12}$ alkanes, preferably of natural origin, in particular linear or branched alkanes, $C_9$-$C_{12}$. This latter mixture is in particular known under the name INCI $C_9$-$C_{12}$ ALCANE E511470, CAS 68608-12-8, VEGELIGHT SILK® marketed by BioSynthIs. This mixture of volatile, biodegradable, volatile oils obtained from coconut oil (viscosity is 0.9-1.1 cSt (40° C.) and a flash point at 65° C.).

The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the hydrocarbon-based liquid fatty substances having an overall solubility parameter according to the Hansen solubility space of less than or equal to 20 (MPa)½, mention may be made of oils, which may be chosen from natural or synthetic, hydrocarbon-based oils, which are optionally branched, alone or as a mixture.

According to a very advantageous embodiment, the dispersion may include one or more liquid fatty substances which are one or more hydrocarbon-based oils. The hydrocarbon-based oil(s) may be volatile or non-volatile. In some embodiments, only a single hydrocarbon-based oil is utilized.

According to a preferred embodiment, the liquid hydrocarbon-based fatty substance(s) are hydrocarbon-based oils which are volatile or are a mixture of different volatile oils.

According to a preferred embodiment, the fatty substance(s) are linear or branched hydrocarbon oils which are volatile in particular chosen from undecane, dodecane, isododecane, tridecane, and their mixture of different, volatile oils preferably comprising isododecane in the mixture, or a mixture of undecane and tridecane.

According to another particular embodiment, the liquid fatty substance (s) are a mixture of a volatile hydrocarbon oil and a non-volatile hydrocarbon oil, the mixture of which preferably comprises dodecane or isododecane as volatile oil.

According to another advantageous embodiment, the fatty substance(s) may be a mixture of non-volatile oil(s) and volatile oil(s), where preferably the volatile oil(s) include undecane, dodecane, isododecane, and/or tridecane, more preferably isododecane. As volatile and non-volatile oil mixture, mention may be made of a mixture of isododecane and isononyl isononanoate.

More preferably when the fatty substance(s) are a mixture of volatile and non-volatile oil, the amount of volatile oil is greater than the amount of non-volatile oil.

According to another particular embodiment, the hydrocarbon-based liquid fatty substance(s) are a mixture of a volatile oil and a non-volatile oil such as an isododecane/octyldodecanol mixture or an isododecane/isononyl isononanoate mixture.

The hydrocarbon-based oil may be chosen from: hydrocarbon-based oils containing from 8 to 14 carbon atoms, and notably:

branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade names Isopar or Permethyl;

linear alkanes, for instance n-dodecane ($C_{12}$) and n-tetradecane ($C_{14}$) sold by Sasol under the references, respectively, Parafol 12-97 and Parafol 14-97, and also mixtures thereof, the undecane-tridecane mixture, mixtures of n-undecane ($C_{11}$) and of n-tridecane ($C_{13}$) obtained in examples 1 and 2 of patent application WO 2008/155,059 from the company Cognis, and mixtures thereof;

hydrocarbon-based oils of plant origin such as triglycerides constituted of fatty acid esters of glycerol, the fatty acids of which may have chain lengths ranging from $C_4$ to $C_{24}$, these chains possibly being linear or branched, and saturated or unsaturated; these oils are notably heptanoic acid or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cotton oil, hazelnut oil, macadamia oil, jojoba oil, alfalfa oil, poppy oil, pumpkin oil, sesame seed oil, marrow oil, rapeseed oil, blackcurrant oil, evening primrose oil, millet oil, barley oil, quinoa oil, rye oil, safflower oil, candlenut oil, passion flower oil or musk rose oil; shea butter; or else caprylic/capric acid triglycerides, for instance those sold by the company Stéarinerie Dubois or those sold under the names Miglyol 810®, 812® and 818®;

Synthetic Ethers Containing from 10 to 40 Carbon Atoms;

linear or branched hydrocarbons of mineral or synthetic origin, such as petroleum jelly, polydecenes, hydrogenated polyisobutene such as Parleam®, squalane and liquid paraffins, and mixtures thereof, esters such as oils of formula R1C(O)—O—R2 in which R1 represents a linear or branched fatty acid residue including from 1 to 40 carbon atoms and R2 represents a, notably branched, hydrocarbon-based chain containing from 1 to 40 carbon atoms, on condition that R1+R2≥10, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2 octyldecyl palmitate, 2-octyldodecyl myristate, alcohol or polyalcohol heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters;

fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2 undecylpentadecanol.

In particular, the dispersion may include at least one liquid hydrocarbon-based fatty substance iii) chosen from:
  plant oils formed by fatty acid esters of polyols, in particular triglycerides, such as sunflower oil, sesame oil, rapeseed oil, macadamia oil, soybean oil, sweet almond oil, beauty-leaf oil, palm oil, grapeseed oil, corn oil, arara oil, cottonseed oil, apricot oil, avocado oil, jojoba oil, olive oil or cereal germ oil;
  linear, branched or cyclic esters containing more than 6 carbon atoms, notably 6 to 30 carbon atoms; and notably isononyl isononanoate;
  and more particularly the esters of formula Rd-C(O)—O—Re in which Rd represents a higher fatty acid residue including from 7 to 19 carbon atoms and Re represents a hydrocarbon-based chain including from 3 to 20 carbon atoms, such as palmitates, adipates, myristates and benzoates, notably diisopropyl adipate and isopropyl myristate;
  hydrocarbons and notably volatile or non-volatile, linear, branched and/or cyclic alkanes, such as $C_5$-$C_{60}$ isoparaffins, which are optionally volatile, such as isododecane, Parleam (hydrogenated polyisobutene), isohexadecane, cyclohexane or Isopars; or else liquid paraffins, liquid petroleum jelly, or hydrogenated polyisobutylene; notably isododecane;
  Ethers Containing 6 to 30 Carbon Atoms;
  aliphatic fatty monoalcohols containing 6 to 30 carbon atoms, the hydrocarbon-based chain not including any substitution groups, such as oleyl alcohol, decanol, dodecanol, octadecanol, octyldodecanol and linoleyl alcohol;
  polyols containing 6 to 30 carbon atoms, such as hexylene glycol; and
  their mixtures, such as the combination of undecane and tridecane such as for example CETIOL UT®, preferably isododecane, or mixtures of linear or branched $C_8$-$C_{10}$ fatty acid esters and $C_{12}$ fatty alcohol $C_6$-$C_{18}$ alkanes resulting from the hydrogenation/complete reduction of mixtures of fatty acids obtained from *Cocos nucifera* oil (coconut), in particular dodecane such as mixtures of cococaprylate/caprate and dodecane, there may be mentioned those of the INCI name coconut alkanes (and) Coco-caprylate/caprate marketed under the name VEGELIGHT 1212LC® by Grant Industries; or mixtures of $C_9$-$C_{12}$ alkanes, the chains of which comprise 9 to 12 carbon atoms, preferably linear or branched, $C_9$-$C_{12}$ alkanes, in particular comprising dodecane, there may be mentioned the mixture of oil from INCI name $C_9$-$C_{12}$ ALKANE, VEGELIGHT SILK® marketed by BioSynthIs.

Advantageously, the hydrocarbon-based liquid fatty substance(s) may be apolar, i.e., formed solely of carbon and hydrogen atoms.

Preferably, the dispersion may include at least one apolar liquid hydrocarbon-based fatty substance iii) preferably chosen from:
  linear or branched C8-C30, in particular C10-C20 and more particularly C10-C16 alkanes, which are volatile or non-volatile, preferably volatile;
  non-aromatic cyclic C5-C12 alkanes, which are volatile or non-volatile, preferably volatile; and
  mixtures thereof.

The liquid hydrocarbon-based fatty substance(s) may preferably be chosen from hydrocarbon-based oils containing from 8 to 16 carbon atoms, in particular containing from 10 to 14 carbon atoms, which are preferably volatile, more particularly the apolar oils, as disclosed herein.

Among the branched C8-C16 and notably C10-C14 alkanes that are suitable for use as liquid hydrocarbon-based fatty substances in the dispersion, mention may be made of:
  isoalkanes of petroleum origin (also known as isoparaffins), such as isododecane (also known as 2,2,4,4,6-pentamethylheptane), isodecane and, for example, the oils sold under the Isopar or Permethyl trade names,
  linear alkanes, for instance n-dodecane (C12) and n-tetradecane (C14) sold by Sasol under the references, respectively, Parafol 12-97 and Parafol 14-97, and also mixtures thereof, the undecane-tridecane mixture, mixtures of n-undecane (C11) and of n-tridecane (C13) from the company Cognis, and
  mixtures thereof.

Preferentially, the liquid hydrocarbon-based fatty substance(s) iii) may be apolar, more particularly isododecane.

According to another advantageous embodiment, the hydrocarbon-based liquid fatty substance(s) are a mixture of non-volatile and volatile oil; preferably, the mixture comprises isododecane as volatile oil or a mixture of oils, notably of undecane and tridecane or else isononyl isononanoate or octyldodecanol.

Preferably, the liquid hydrocarbon-based fatty substance(s) may be present in the dispersion of the invention in an amount of between 1% and 25% by weight, more preferentially between 2.5% and 20% by weight, even more preferentially between 4% and 15% and preferentially between 10% and 11.2% by weight relative to the total weight of the dispersion, where the dispersion may include water.

According to a particular embodiment of the invention, the liquid hydrocarbon-based fatty substance(s) may be present in the dispersion of the invention in an amount of between 1.5% and 30% by weight, more preferentially between 4% and 20% by weight, even more preferentially between 8% and 15% and notably between 12% and 13% by weight relative to the total weight of the dispersion, where the dispersion is free of water.

According to a particular embodiment of the invention, the one or more volatile hydrocarbons may be present from about 1 to about 85 wt. % based on the total weight of the cosmetic composition. In some instances, the cosmetic composition may include at least one or more volatile hydrocarbons chosen from isoparaffin, isohexadecane, isododecane, isodecane, undecane, tridecane, dodecane, isohexyl, isodecyl, neopentanoate, or a combination thereof. In at least one instance, isododecane and/or isoparaffins (e.g., C8-9 isoparaffin) are preferred. The cosmetic composition may be formulated to include volatile hydrocarbons that contain no silicon atoms.

The total amount of the volatile hydrocarbon may vary. In some embodiments, the cosmetic composition may include about 1 to about 85 wt. % based on the total weight of the cosmetic composition. In some cases, the total amount of volatile hydrocarbons is about 5 to about 85 wt %, about 10 to about 85 wt %, about 12 to about 85 wt %, about 14 to about 85 wt %, about 15 to about 85 wt %, about 20 to about 85 wt. %, about 30 to about 85 wt. %, about 1 to about 80 wt. %, about 5 to about 80 wt. %, about 10 to about 80 wt. %, about 15 to about 80 wt. %, about 20 to about 80 wt. %, based on the total weight of the cosmetic composition. In some cases, the total amount of volatile hydrocarbons is about 30 to about 80 wt. %, about 30 to about 75 wt. %; about 35 to about 85 wt. %, about 35 to about 80 wt. %, about 35 to about 75 wt. %; about 40 to about 85 wt. %, about 40 to about 80 wt. %, about 40 to about 75 wt. %; about 45 to about 85 wt. %, about 45 to about 80 wt. %, about 45 to about 75 wt. %; about 50 to about 85 wt. %, about 50 to about 80 wt. %, about 50 to about 75 wt. %; about 55 to about 85 wt. %, about 55 to about 80 wt. %, about 55 to about 75 wt. %; about 60 to about 85 wt. %, about 60 to about 80 wt. %, about 60 to about 75 wt. %; about 65 to about 85 wt. %, about 65 to about 80 wt. %, or about 65 to about 75 wt. %, including ranges and subranges thereof, based on the total weight of the cosmetic composition.

According to a particular embodiment of the invention, the mass ratio of the sum of the ingredients ([% by weight of ethylenic polymeric core particles+% by weight of polymeric stabilizing agents]/% by weight of fatty substance that is liquid at 20° C. and 1 atmosphere) is less than or equal to 3, more particularly the mass ratio is between 1 and 2.5, even more particularly between 1.5 and 2.4, preferentially between 1.7 and 2.2.

The dispersion may optionally include other components. For example, in some embodiments, the dispersion may include one or more polyols that are liquid at 20° C. and 1 atm, and/or may include water.

Polyol(s)

The dispersion may optionally include one or more polyols that are liquid at 20° C. and 1 atm.

The term "polyol" means a compound which is liquid at 20° C. and 1 atm, comprising at least 2 hydroxyl groups, preferably between 2 and 10 hydroxyl groups (OH), and comprising at least one carbon atom. Particularly, the polyol(s) of the invention are chosen from compounds comprising at least 2 OH groups, preferably between 2 and 8 OH groups, more preferentially 2 or 3 OH groups, even more preferentially 3 OH groups, and comprising a linear or branched, cyclic or acyclic, saturated or unsaturated hydrocarbon-based chain comprising from 1 to 10 carbon atoms, in particular between 2 and 8 carbon atoms.

More particularly, the polyol(s) of the instant disclosure have a molecular weight of between 50 g/mol and 300 g/mol, more particularly between 80 g/mol and 150 g/mol.

According to a particular embodiment of the instant disclosure, the polyol(s) are chosen from:

hydrocarbon-based (C2-C6)alkanediol compounds and (C2-C6)alkanetriol such as glycerol and butanetriols, and pentanetriols, and hexanetriols such as hexane-1,2,6-triol.

Preferentially, the polyol(s) iv) are chosen from (C2-C6) alkanetriol hydrocarbon-based compounds such as glycerol.

According to one embodiment, the dispersion may include one or more polyols in an amount of greater than or equal to 5% by weight and less than 95% by weight relative to the total weight of the dispersion free of water; in particular, the amount of polyol(s) in the dispersion is between 10% and 90% by weight relative to the total weight of the dispersion free of water, more particularly between 25% and 90% by weight, more particularly between 35% and 90% by weight, relative to the total weight of the dispersion free of water; and more preferentially between 50% and 70%.

According to one embodiment, the dispersion may include one or more polyols in an amount of greater than or equal to 15% by weight and less than 90% by weight relative to the total weight of the dispersion with water; in particular, the amount of polyol(s) in the dispersion is between 20% and 85% by weight relative to the total weight of the dispersion with water, more particularly between 25% and 80% by weight, more particularly between 40% and 60% by weight, relative to the total weight of the dispersion including water.

In some instances, the cosmetic composition may include one or more polyols, in addition to the one or more polyol(s) incorporated into the dispersion, which may be the same or different than the ones discussed here.

According to one embodiment, the one or more polyols may be present from about 1 to about 50 wt. % based on the total weight of the skin tightening composition. The total amount of the polyols may vary but is typically about 1 to about 50 wt. % based on the total weight of the skin tightening composition. In some cases, the total amount of polyols is from about 1, 2, 3, 4, 5, 6, 7, 8, 9, 10, 12, 14, 16, 18, 20, 22, 24 to about 24, 25, 26, 27, 28, 29, 30, 31, 32, 33, 34, 35, 36, 38, 40, 42, 44, 46, 48, and to 50 wt. % based on the total weight of the cosmetic composition. In some embodiments of the cosmetic composition, the weight ratio of the total amount of the polymeric core of the dispersion to the total amount of the amount of polyols is between around 1:1 to 4:1. In one or more embodiments of the cosmetic composition, the weight ratio of the total amount of the polymeric core of the dispersion to the total amount of the amount of polyols is 1:1 to 4:1, 1:1 to 3.5:1, 1:1 to 3:1, 1:1 to 2.5:1, 1:1 to 2:1, 1:1 to 1.5:1, or any ranges and subranges thereof.

Water

In some embodiments, the dispersion, notably the hydrogel, may comprises water in an amount of between 5% and 50% by weight relative to the total weight of the dispersion, more particularly between 7% and 48% by weight and preferentially between 9% and 46% by weight relative to the total weight of the dispersion.

In some embodiments, the weight ratio of the hydrocarbon-based liquid fatty substance(s)/the water is between 0.1 and 5, more particularly between 0.2 and 1, preferably between 0.3 and 0.7, more preferentially between 0.4 and 0.6.

The water that is suitable for use in the instant disclosure may be tap water, distilled water, spring water, a floral water such as cornflower water and/or a mineral water such as Vittel water, Lucas water or La Roche Posay water and/or a thermal water.

The dispersion may also comprise one or more water-miscible solvents. According to the instant disclosure, the term "water-miscible solvent" denotes a compound that is liquid at room temperature and water-miscible (miscibility with water of greater than 50% by weight at 25° C. and atmospheric pressure). The water-miscible solvents that may be used in dispersion of the instant disclosure may also be volatile. Among the water-miscible solvents that may be used in the composition according to the invention, mention may notably be made of lower monoalcohols containing from 2 to 5 carbon atoms such as ethanol and isopropanol.

The water may also comprise any water-soluble or water-dispersible compound that is compatible with an aqueous phase, such as associated film-forming polymers, surfactants, and mixtures thereof. The term "surfactant" means a "surface agent", which is a compound that is capable of modifying the surface tension between two surfaces; surfactants are amphiphilic molecules, i.e. they contain two parts of different polarity, one lipophilic and apolar, and the other hydrophilic and polar. The surfactants may be non-ionic, anionic, amphoteric or cationic active agents.

In some embodiments, the dispersion may not comprise more than 3% by weight of surfactants relative to the total weight of the dispersion, preferentially not more than 2% by weight of surfactants relative to the total weight of the dispersion, more particularly not more than 1% by weight of surfactants relative to the total weight of the dispersion; even more preferentially, the composition does not comprise more than 0.5% by weight of surfactants relative to the total weight of the dispersion, and better still the mixture does not comprise any surfactant.

In some embodiments, the dispersion includes 10-20% of the ethylenic polymeric core particles, 15-35% of the hydrocarbon-based liquid fatty substance(s) 10-30% of the polymeric stabilizer, and 40-60% of water, by weight relative to the total weight of the dispersion.

Transfer Resistant Film Former.

In some embodiments, the cosmetic composition may include a transfer-resistant film former. The term "film former" is understood to mean a polymer which is capable of forming, by itself alone or in the presence of an additional film-forming agent, a macroscopically continuous film on a support, in particular on keratin substances, and preferably a cohesive film.

In some embodiments, the cosmetic composition comprises or consists of a silicone-based film former. In some embodiments, the transfer-resistant film former may include a silicone pullulan, a silicone norbornene, a pseudo block copolymer, a MQ resin, a T propyl siloxane resin, a MQT resin, or a combination thereof. In some embodiments, the transfer-resistant film former may include a MQ resin, a polyester, a trimethylsiloxymethacrylate copolymer, and/or a dimethicone copolymer.

In some embodiments, the film former(s) may be present in a total amount of 1%-30% by weight of the composition. In some embodiments, the film former(s) may be present in a total amount of 1%-5% by weight. In some embodiments, the film former(s) may be present in a total amount of 5%-20% by weight. In some embodiments, the film former(s) may be present in a total amount of 5%-10% by weight. In some embodiments, the film former(s) may be present in a total amount of 8%-14% by weight.

Pseudo Block Copolymer

As used herein, the term "pseudo block copolymer" refers to a film-forming block polymer, preferably containing at least one first block and at least one second block having different glass transition temperatures (Tg), the first and second blocks being joined together by an intermediate block comprising at least one monomer that is a constituent of the first block and at least one monomer that is a constituent of the second block. Advantageously, the first and second blocks of the block polymer are mutually incompatible with one another. Polymers of this kind are described for example in documents EP 1411069 or WO04/028488. In some embodiments, the pseudo-block polymer has a polydispersity index (I) of greater than 2.

In some embodiments, the film-forming block polymer is a film-forming linear ethylenic block polymer. As used herein, the term "mutually incompatible" blocks means that the mixture formed from the polymer corresponding to the at least one first block and the polymer corresponding to the at least one second block is immiscible in the polymerization solvent that is of the majority amount by weight of the at least one pseudo-block polymer, at room temperature (25° C.) and atmospheric pressure ($10^5$ Pa), for a polymer mixture content of greater than or equal to 5% by weight, relative to the total weight of the mixture (polymers and solvent), wherein:

i) the polymers corresponding to the at least one first and at least one second blocks are present in the mixture in an amount such that the respective weight ratio ranges from 10:90 to 90:10 and ii) each of the polymers corresponding to the at least one first and at least one second blocks has an average (weight-average or number-average) molecular mass equal to that of the at least one pseudo-block polymer 15%.

In some embodiments, the transfer-resistant film former may be a silicone resins that may be, e.g., of MQ type, of T type (especially a t-propyl siloxane resin), and/or of MQT type. In some embodiments, a combination of an MQ type resin and a T-type resin may be utilized. In some embodiments, a combination of a MQ type resin and a MQT type resin may be utilized. In some embodiments, a combination of a T-type resin and a MQT type resin may be utilized. In some embodiments, a combination of a MQ type resin, a T-type resin, and a MQT type resin may be utilized.

MQ Type Resins

As examples of silicone resins of MQ type, mention may be made of the alkyl siloxysilicates of formula $[(R1)_3SiO_{1/2}]_x(SiO_{4/2})_y$ (MQ units) in which x and y are integers ranging from 50 to 80, and such that the group R1 represents a radical as defined previously, and is preferably an alkyl group containing from 1 to 8 carbon atoms, preferably a methyl group. In some embodiments, the MQ type resin is a trimethylsiloxysilicate.

As examples of solid silicone resins of MQ type of trimethylsiloxysilicate type, mention may be made of those sold under the reference SR1000 by the company General Electric, under the reference TMS 803 by the company Wacker, or under the name KF-7312J by the company Shin-Etsu or DC749 or DC593 by the company Dow Corning.

As silicone resins comprising MQ siloxysilicate units, mention may also be made of phenylalkylsiloxysilicate resins, such as phenylpropyldimethylsiloxysilicate (Silshine 151 sold by the company General Electric). The preparation of such resins is described especially in U.S. Pat. No. 5,817,302.

T Type Resins.

Examples of these silicone resins of type T that may be mentioned include the polysilsesquioxanes of formula $(RSiO_{3/2})_x$ (units T) in which x is greater than 100 and such that the group R is an alkyl group containing from 1 to 10 carbon atoms, the said polysilsesquioxanes also possibly comprising Si—OH end groups. In some embodiments, the T-type resin is a polymethylsilsesquioxane. In some embodiments, the T-type resin is polypropylsilsesquioxane.

Polymethylsilsesquioxane resins that may preferably be used are those in which R represents a methyl group, for instance those sold:

by the company Wacker under the reference Resin MK, such as Belsil PMS MK: polymer comprising $CH_3SiO_{3/2}$ repeating units (units T), which may also comprise up to 1% by weight of $(CH_3)_2SiO_{2/2}$ units (units D) and having an average molecular weight of about 10,000 g/mol, or by the company Shin-Etsu under the reference KR-220L, which are composed of units T of formula $CH_3SiO_{3/2}$ and have Si—OH (silanol) end groups, under the reference KR-242A, which comprise 98% of units T and 2% of dimethyl units D and have Si—OH end groups, or alternatively under the reference KR-251 comprising 88% of units T and 12% of dimethyl units D and have Si—OH end groups.

MQT Type Resins

Resins comprising MQT units that are especially known are those mentioned in document U.S. Pat. No. 5,110,890. A preferred form of resins of MQT type are MQT-propyl (also known as MQTPr) resins. Such resins that may be used in the compositions according to the invention are especially the resins described and prepared in patent application WO 2005/075,542, the content of which is incorporated herein by reference.

In some embodiments, the MQT resin comprises polymethylsilsesquioxane. In some embodiments, the MQT resin may be trimethylsiloxysilicate polymethylsilsesquioxane.

The MQT-propyl resin preferably comprises the following units:

$(R1_3SiO_{1/2})_a$ (i)

$(R2_2SiO_{2/2})_b$ (ii)

$(R3SiO_{3/2})_c$ and (iii)

$(SiO_{4/2})_d$ (iv)

with R1, R2 and R3 independently representing a hydrocarbon-based radical (especially alkyl) containing from 1 to 10 carbon atoms, a phenyl group, a phenylalkyl group or a hydroxyl group, and preferably an alkyl radical containing from 1 to 8 carbon atoms or a phenyl group, a being between 0.05 and 0.5, b being between 0 and 0.3, c being greater than 0, d being between 0.05 and 0.6, a+b+c+d=1, and a, b, c and d being mole fractions, on condition that more than 40 mol % of the groups R3 of the siloxane resin are propyl groups.

Preferably, the siloxane resin comprises the following units:

$(R1_3SiO_{1/2})_a$ (i)

$(R3SiO_{3/2})$, and (iii)

$(SiO_{4/2})_d$ (iv)

with R1 and R3 independently representing an alkyl group containing from 1 to 8 carbon atoms, R1 preferably being a methyl group and R3 preferably being a propyl group, a being between 0.05 and 0.5 and preferably between 0.15 and 0.4, c being greater than 0 and preferably between 0.15 and 0.4, d being between 0.05 and 0.6, preferably between 0.2 and 0.6, or alternatively between 0.2 and 0.55, a+b+c+d=1 and a, b, c and d being mole fractions, on condition that more than 40 mol % of the groups R3 of the siloxane resin are propyl groups.

In some embodiments, the siloxane resins that may be used according to the invention may be obtained via a process comprising the reaction of: A) an MQ resin comprising at least 80 mol % of units $(R1_3SiO_{1/2})_a$ and $(SiO_{4/2})_d$, R1 representing an alkyl group containing from 1 to 8 carbon atoms, an aryl group, a carbinol group or an amino group, a and d being greater than 0, the ratio a/d being between 0.5 and 1.5; and B) a T-propyl resin comprising at least 80 mol % of units $(R3SiO_{3/2})_c$, R3 representing an alkyl group containing from 1 to 8 carbon atoms, an aryl group, a carbinol group or an amino group, c being greater than 0, on condition that at least 40 mol % of the groups R3 are propyl groups, in which the mass ratio A/B is between 95/5 and 15/85 and the mass ratio A/B is preferably 30/70. Advantageously, the mass ratio A/B is between 95/5 and 15/85. Preferably, the ratio A/B is less than or equal to 70/30. These preferred ratios have been proven to produce deposits that are comfortable due to the absence of percolation of the rigid MQ resin particles in the deposit.

In some embodiments, the silicone resin is chosen from the group comprising:

a) a resin of MQ type, chosen especially from (i) alkyl siloxysilicates, which may be trimethyl siloxysilicates, of formula $[(R1)_3SiO_{1/2}]_x(SiO_{4/2})_y$, in which x and y are integers ranging from 50 to 80, and such that the group R1 represents a hydrocarbon-based radical containing from 1 to 10 carbon atoms, a phenyl group, a phenylalkyl group or a hydroxyl group, and preferably is an alkyl group containing from 1 to 8 carbon atoms, preferably a methyl group, and (ii) phenylalkyl siloxysilicate resins, such as phenylpropyldimethyl siloxysilicate, and/or b) a resin of T type, chosen especially from the polysilsesquioxanes of formula $(RSiO_{3/2})_x$, in which x is greater than 100 and the group R is an alkyl group containing from 1 to 10 carbon atoms, for example a methyl group, or a t-propyl group, the said polysilsesquioxanes also possibly comprising Si—OH end groups, and/or c) a resin of MQT type, especially of MQT-propyl type, which may comprise units (i) $(R1_3SiO_{1/2})_a$, (ii) $(R2_2SiO_{2/2})_b$, (iii) $(R3SiO_{3/2})_c$ and (iv) $(SiO_{4/2})_d$, with R1, R2 and R3 independently representing a hydrocarbon-based radical, especially alkyl, containing from 1 to 10 carbon atoms, a phenyl group, a phenylalkyl group or a hydroxyl group and preferably an alkyl radical containing from 1 to 8 carbon atoms or a phenyl group, a being between 0.05 and 0.5, b being between 0 and 0.3, c being greater than 0, d being between 0.05 and 0.6, a+b+c+d=1, and a, b, c and d being mole fractions, on condition that more than 40 mol % of the groups R3 of the siloxane resin are propyl groups.

Polyester.

In some embodiments, the polyesters may be selected from those which include a backbone derived from the reaction of at least one diol and at least one diacid. The diol may be a linear or branched aliphatic dihydric compound having two —OH groups. The diacid may be a linear or branched chain aliphatic dicarboxylic acid having two —COOH groups, although aromatic acids may also be used. The polyester backbone may be derived from the co-condensation of such diols and diacids. The diol may contain from 2 to 10 ether linkages (—R—O—R—) or from 2 to 10 tertiary amine groups ($NR_3$). The polyester may be linear or crosslinked. In some embodiments, the polyester resin may be a saturated crosslinked hydroxy functional; polyester, comprised of glycerin, diethylene glycol, adipate crosslinked polymer, also known in its INCI designation as adipic acid/diethylene glycol/glycerin crosspolymer, sold as Lexorez® 100 by the Inolex Chemical Company. In some embodiments, the polyester resin is comprised of hexanedioic acid, 1,2,3-propanediol, 2,2,4 trimethyl-1,3-pentanediol crosslinked polymer, also known in its INCI designation as trimethylpentanediol/adipic acid/glycerin crosspolymer, sold as Lexorez® 200.

Hydrophilic Active Agent.

In some embodiments, the cosmetic composition may include a hydrophilic active agent. In some embodiments, the hydrophilic active agent may be incorporated into the at least one ethylenic polymeric core formed by the polymers disclosed herein. In some embodiments, the hydrophilic active agent may be external to the ethylenic polymeric core.

In some embodiments, the hydrophilic active agent may be:
- a moisturizing agent, such as a polyol such as, for example, glycerin and sugars, urea and its derivatives, such as in particular hydroxyalkyl urea, in particular hydroxyalkylurea, and mixtures thereof;
- a desquamating agent, which may be a compound capable of acting either directly on desquamation by promoting exfoliation, such as β-hydroxy acids, in particular salicylic acid and its derivatives (including 5-n-octanoylsalicylic acid); α-hydroxy acids, such as glycolic acid, citric acid, lactic acid, tartaric acid, malic acid or mandelic acid; urea; gentisic acid; oligofucoses; cinnamic acid; extract of *Sophora japonica*, resveratrol and certain jasmonic acid derivatives; or acting on the enzymes involved in the desquamation or degradation of corneodesmosomes, glycosidases, stratum corneum chymotryptic enzyme (SCCE), or even other proteases (trypsin, chymotrypsin-like). Mention may be made of agents for chelating mineral salts: EDTA, N-acyl-N,N', N'-ethylenediaminetriacetic acid; aminosulfonic compounds and in particular (N-2-hydroxyethylpiperazine-N-2-ethane)sulfonic acid (HEPES); 2-oxothiazolidine-4-carboxylic acid (procysteine) derivatives; α-amino acid derivatives of the type such as glycine (as described in EP-0 852 949 and sodium methylglycinediacetate sold by BASF under the trade name Trilon M); honey; sugar derivatives such as O-octanoyl-6-D-maltose and N-acetylglucosamine;
- a Humectant;
- an anti-aging agent, which may include, for example, one or more of C-beta-D-xylopyranoside-2-hydroxypropane (Pro-Xylane), retinol, peptides, caffeine, and other components that provide improvement to skin texture, any other suitable soluble/dispersible targeted active ingredient, and combinations thereof.
- a Healing Agent;
- an antimicrobial agent, non-limiting examples of which include 2,4,4'-trichloro-2'-hydroxydiphenyl ether (or triclosan), 3,4,4'-trichlorobanilide, phenoxyethanol, phenoxypropanol, phenoxyisopropanol, hexamidine isethionate, metronidazole and its salts, micronazole and its salts, itraconazole, terconazole, econazole, ketoconazole, saperconazole, fluconazole, clotrimazole, butoconazole, oxiconazole, sulfaconazole, sulconazole, terbinafine, ciclopirox, ciclopiroxolamine, undecylenic acid and its salts, benzoyl peroxide, 3-hydroxybenzoic acid, 4-hydroxybenzoic acid, phytic acid, N-acetyl-L-cysteine acid, lipoic acid, azelaic acid and its salts, arachidonic acid, resorcinol, 2,4,4'-trichloro-2'-hydroxydiphenyl ether, 3,4,4'-trichlorocarbanilide, octopirox, octoxyglycerine, octanoylglycine, caprylyl glycol, 10-hydroxy-2-decanoic acid, dichlorophenylimidazole dioxolane and its derivatives described in patent WO 93/18743, farnesol and phytosphingosines, and mixtures thereof;
- a Water-Soluble Texture Modifier;
- a water-soluble colorant such as beetroot juice or caramel;
- a pigment modifying agent and/or skin lightening agents, such as double-stranded RNA oligonucleotides are useful for decreasing tyrosinase expression. Mention may also be made of ceramides, vitamin C and derivatives thereof, in particular vitamin CG, CP and 3-O ethyl vitamin C, alpha- and beta-arbutin, ferulic acid, kojic acid, resorcinol and derivatives thereof, calcium D-pantethine sulphonate, lipoic acid, ellagic acid, vitamin B3, phenylethyl resorcinol, for instance Symwhite 377® from the company Symrise, a kiwi fruit (*Actinidia chinensis*) juice sold by Gattefosse, an extract of *Paeonia suffructicosa* root, such as the product sold by the company Ichimaru Pharcos under the name Botanpi Liquid B®, an extract of brown sugar (*Saccharum officinarum*), such as the extract of molasses sold by the company Taiyo Kagaku under the name Molasses Liquid, a mixture of undecylenic acid and undecylenoyl phenyl alanine, such as Sepiwhite MSH® from Seppic;
- a vitamin such as vitamin B3, vitamin C, and/or derivatives thereof;
- a swelling agent such as polyols or water; or
- a combination thereof.

The cosmetic composition may also include other components, such as water, a colorant, an antioxidant, an ultraviolet (UV) filter, a mattifying agent, or a combination thereof.

Colorants

The colorants that may be incorporated into the composition (but not incorporated into the polymeric cores), may include pigments, dyes, such as liposoluble dyes, nacreous pigments, and pigments with special effects, and/or pearlescent agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow. The liposoluble dyes, when present, generally have a concentration ranging up to 40% by weight of the total weight of the composition, such as from 0.0001% to 30%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.0001% to 40%, preferably from 0.001% to 30%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

As used herein, the term "pigment" refers to any pigment that gives color to keratin materials, of synthetic or natural origin, the solubility of the pigments in water at 25° C. and at atmospheric pressure (760 mmHg) being less than 0.05% by weight and preferably less than 0.01%;

As used herein, the term "lake" refers to dyes adsorbed onto insoluble particles, the assembly thus obtained remaining insoluble during use. The inorganic substrates onto which the dyes are adsorbed are, for example, alumina, silica, calcium sodium borosilicate or calcium aluminum borosilicate and aluminum. Among the organic dyes, mention may be made of cochineal carmine.

As used herein, the term "pigments with special effects" refers to pigments that generally create a colored appearance (characterized by a certain shade, a certain vivacity and a certain level of luminance) that is non-uniform and that changes as a function of the conditions of observation (light, temperature, angles of observation, etc.). They thereby differ from colored pigments, which afford a standard uniform opaque, semi-transparent or transparent shade. In some embodiments, the pigment with special effects may include those with a low refractive index, such as fluorescent, photochromic or thermochromic pigments, and those with a higher refractive index, such as nacres or glitter flakes.

In some embodiments, the colorants may be present in the composition in a concentration ranging up to 50% by weight of the total weight of the composition, such as from 0.0001% to 40%, and further such as from 0.001% to 30%, including all ranges and subranges therebetween. In the case of certain products, the pigments, including nacreous pigments, may, for example, represent up to 50% by weight of the composition such as, for example, from 6% to 50% of the composition.

Antioxidants may be incorporated into the composition. In some embodiments, the antioxidant is incorporated into the polymeric cores. In some embodiments, the antioxidant is not incorporated into the polymeric cores. In some embodiments, the antioxidant may be present within the cores and outside of the cores. The antioxidants may include tocopherol and esters thereof, in particular tocopheryl acetate; EDTA, ascorbic acid and derivatives thereof, in particular magnesium ascorbyl phosphate and ascorbyl glucoside; chelating agents, such as BHT, BHA, N,N'-bis(3,4,5-trimethoxybenzyl)ethylenediamine and its salts, and mixtures thereof.

The cosmetic composition may include an ultraviolet (UV) filter incorporated into the composition (but not incorporated into the polymeric cores). The UV filter may include, e.g., an aminobenzoic acid derivative, a dibenzoylmethane derivative, a salicylic acid derivative, a cinnamic derivative, a β,β diphenylacrylate derivative, a benzophenone derivative, benzylidene camphor derivative, and mixtures thereof. Mention may be made especially of ethylhexyl methoxycinnamate sold under the tradename UVINUL MC 80® by the company BASF, of ethylhexyl salicylate sold under the tradename NEO HELIOPAN OS® by the company SYMRISE and of octocrylene sold under the tradename NEO HELIOPAN 303® by the company SYMRISE.

The cosmetic composition may include a mattifying agent, which may include, but is not limited to, mattifying fillers such as, for example, talc, silica, silicone elastomers, and polyamides, and waxes such as, for example, beeswax and copernicia cerifera (carnauba) wax.

Example 1

Cosmetic lip formulations were manufactured, using the compositions shown below.

TABLE 1

(Control Formulations, amounts in wt % of active)

| Material | 1 | 2 | 3 | 4 | 5 | 6 |
|---|---|---|---|---|---|---|
| Dispersion | ~20 | | | | | |
| Acrylates/Dimethicone Copolymer | | ~20 | | | | |
| Acrylates/Polytrimethyl siloxymethacrylate Copolymer | | | ~20 | | | |
| Trimethylsiloxysilyl Carbamoyl Pullulan | | | | ~20 | | |
| Norbornene/Tris (Trimethylsiloxy) Silylnorbornene Copolymer | | | | | ~20 | |
| Acrylic Acid/Isobutyl Acrylate/Isobornyl Acrylate Copolymer | | | | | | ~20 |
| Pigment | ~2 | ~2 | ~2 | ~2 | ~2 | ~2 |
| Trihydroxystearin | ~3 | ~3 | ~3 | ~3 | ~3 | ~3 |
| Isododecane | q.s. | q.s. | q.s. | q.s. | q.s. | q.s. |

TABLE 2

(Exemplary Formulations, amounts in wt % of active)

| Material | 7 | 8 | 9 | 18 | 11 |
|---|---|---|---|---|---|
| Dispersion | ~10 | ~10 | ~10 | ~10 | ~10 |
| Acrylates/Dimethicone Copolymer | ~10 | | | | |
| Acrylates/Polytrimethyl siloxymethacrylate Copolymer | | ~10 | | | |
| Trimethylsiloxysilyl Carbamoyl Pullulan | | | ~10 | | |
| Norbornene/Tris (Trimethylsiloxy) Silylnorbornene Copolymer | | | | ~10 | |
| Acrylic Acid/Isobutyl Acrylate/Isobornyl Acrylate Copolymer | | | | | ~10 |
| Pigment | ~2 | ~2 | ~2 | ~2 | ~2 |
| Trihydroxystearin | ~3 | ~3 | ~3 | ~3 | ~3 |
| Isododecane | q.s. | q.s. | q.s. | q.s. | q.s. |

TABLE 3

(Evaluation Scores)

| Material | Sample | Oil | Oil Cotton pad | Saliva | Saliva Cotton | Acetic Acid | A.A. Cotton | Caliper Swelling |
|---|---|---|---|---|---|---|---|---|
| Dispersion | 1 | 1 | 2 | 2.63 | 3 | 1 | 1.63 | 0.077 |
| Acrylates/Dimethicone Copolymer | 2 | 1 | 2.5 | 1 | 1.25 | 1 | 1.25 | N/A |
| Acrylates/Polytrimethyl siloxymethacrylate Copolymer | 3 | 1 | 1.75 | 1 | 1.13 | 1 | 1.25 | N/A |
| Trimethylsiloxysilyl Carbamoyl Pullulan | 4 | 1 | 1.75 | 1 | 1.13 | 1 | 1.25 | N/A |

TABLE 3-continued (Evaluation Scores)

| Material | Sample | Oil | Oil Cotton pad | Saliva | Saliva Cotton | Acetic Acid | A.A. Cotton | Caliper Swelling |
|---|---|---|---|---|---|---|---|---|
| Norbornene/Tris (Trimethylsiloxy) Silylnorbornene Copolymer | 5 | 1 | 1.5 | 1.13 | 1 | 1 | 1.13 | N/A |
| Acrylic Acid/Isobutyl Acrylate/Isobornyl Acrylate Copolymer | 6 | 1 | 1.25 | 1 | 1 | 1 | 1.25 | N/A |
| Dispersion + Acrylates/ Dimethicone Copolymer | 7 | 1 | 2 | 2.75 | 2.25 | 1 | 2 | 0.036 |
| Dispersion + Acrylates/ Polytrimethyl Siloxymethacrylate Copolymer | 8 | 1 | 1.75 | 2 | 1.75 | 1 | 1.75 | 0.022 |
| Dispersion + Trimethylsiloxysilyl carbamoyl Pullulan | 9 | 1 | 1.5 | 1.25 | 1.38 | 1 | 1.5 | −0.006 |
| Dispersion + Norbornene/Tris (Trimethylsiloxy) Silylnorbornenecopolymer | 10 | 1 | 1.25 | 1.5 | 1.25 | 1.25 | 1.25 | 0.016 |
| Dispersion + Acrylic Acid/ Isobutyl Acrylate/ Isobornyl Acrylate Copolymer | 11 | 1 | 1.25 | 1.63 | 1.5 | 1 | 1.75 | 0.008 |

As seen in Table 3, solvent resistance was evaluated. Solvent resistance Each formulation was applied to several Black Scrub Panels P121-10N #5015 byko-chart using a 1 mil drawdown bar applicator. The films were allowed to dry overnight at 35° C. and 60% RH. To evaluate the samples, 6 drops of fluids (two drops of olive oil, two drops of artificial saliva, and two drops of 2% acetic acid) were placed on different sections of the film, and then allowed to stand for 10 minutes. The amount of material removed by the drops themselves was evaluated. In addition, a cotton pad was used to gently wipe off each drop 15 times. It was then observed how much product wipes onto the cotton pad and how/if the product moves on the byko-chart substrate. The ratings used a scale of 0 (no removal) to 3 (substantial removal).

As seen, sample 1 (dispersion only) performed the worst of all samples. Samples 2-6 (no dispersion, one of 5 different film formers used) generally had very good resistance, with some exceptions for the oil resistance after wiping with a cotton pad.

The surprising benefit of combining the dispersion with the film formers can be seen by comparing the evaluations for samples 2 vs 7, 3 vs 8, 4 vs 9, 5 vs 10, and 6 vs 11, while keeping the dispersion-only sample (sample 1) in mind.

For example, looking at the Olive Oil evaluations using a cotton pad, it can be seen that the combined samples performed as good or better than the best comparative sample (dispersion-only or film-former only). See Table 4, below. Given the roughly 50/50 combination of dispersion and film-former in the combined samples, it would be expected that the performance would be the midpoint of the two comparative samples. For example, for the combined dispersion (evaluation rating of 2)+Acrylates/Dimethicone Copolymer (evaluation rating of 2.5), it would be expected that the combination would have an evaluation of 2.25. However, the rating was 2—equal to the best performing comparative formula. Thus, the combination of dispersion + transfer-resistant film formers is surprisingly synergistic

TABLE 4

(Oil KW scores)

| Dispersion only score (Sample #) | Film Former Only score (Sample #) | Combined score (Sample #) |
|---|---|---|
| 2 (1) | 2.5 (2) | 2 (7) |
| 2 (1) | 1.75 (3) | 1.75 (8) |
| 2 (1) | 1.75 (4) | 1.5 (9) |
| 2 (1) | 1.5 (5) | 1.25 (10) |
| 2 (1) | 1.25 (6) | 1.25 (11) |

Swelling was also evaluated. Specifically, a 3 mL, drawdown was cast on abrasion paper and dried on bench overnight at ambient temperature. The film thickness was then measured at four distinct areas on the drawdowns using a Mitutoyo caliper as a control. To the samples, ~0.25 grams of deionized water was added to initiate the swelling. After the water was absorbed or evaporated from the top of the film (typically ~1.5 hours), the thickness was again measured using the caliper. The difference (in mm) is the caliper-based "swelling" measurements shown in Table 3.

It can be seen that Sample 1—the dispersion alone—swells substantially. The combinations with many film formers significantly reduces the swelling, and in one case (sample 9) actually reduces the thickness of the film. Surprisingly, at least two compositions (samples 7 and 8) provide significant wear resistance, but also still allow for substantial swelling (e.g., greater than or equal to 0.02 mm).

Example 2

Cosmetic lip formulations were manufactured, using the compositions shown below.

TABLE 5

(Control Formulations, amounts in wt % of active)

| Material | 12 | 13 | 14 | 15 | 16 |
|---|---|---|---|---|---|
| Dispersion | | | | | |
| MQ Resin | ~20 | | | | |
| MQT Resin | | ~20 | | | |
| MQ Resin + T-Propyl Resin | | | ~20 | | |
| MQT Resin + MQ Resin + T-Propyl Resin | | | | ~20 | |
| Polyester | | | | | ~20 |
| Pigment | ~2 | ~2 | ~2 | ~2 | ~2 |
| Trihydroxystearin | ~3 | ~3 | ~3 | ~3 | ~3 |
| Isododecane | q.s. | q.s. | q.s. | q.s. | q.s. |

TABLE 6

(Exemplary Formulations, amounts in wt % of active)

| Material | 16 | 17 | 18 | 19 | 20 |
|---|---|---|---|---|---|
| Dispersion | ~10 | ~10 | ~10 | ~10 | ~10 |
| MQ Resin | ~10 | | | | |
| MQT Resin | | ~10 | | | |
| MQ Resin + T-Propyl Resin | | | ~10 | | |
| MQT Resin + MQ Resin + T-Propyl Resin | | | | ~10 | |
| Polyester | | | | | ~10 |
| Pigment | ~2 | ~2 | ~2 | ~2 | ~2 |
| Trihydroxystearin | ~3 | ~3 | ~3 | ~3 | ~3 |
| Isododecane | q.s. | q.s. | q.s. | q.s. | q.s. |

TABLE 7

(Evaluation Scores)

| Material | Sample | Oil | Oil Cotton | Saliva | Saliva Cotton | Acetic Acid | A.A. Cotton | Caliper Swelling |
|---|---|---|---|---|---|---|---|---|
| Dispersion | 1 | 1 | 2 | 2.63 | 3 | 1 | 1.63 | 0.077 |
| MQ Resin | 12 | 1.00 | 2.25 | 1.00 | 1.00 | 1.00 | 1.63 | N/A |
| MQT Resin | 13 | 1.25 | 2.50 | 1.00 | 1.13 | 1.00 | 1.25 | N/A |
| MQ Resin + T-Propyl Resin | 14 | 1.13 | 2.63 | 1.00 | 1.00 | 1.00 | 1.25 | N/A |
| MQT Resin + MQ Resin + T-Propyl Resin | 15 | 1 | 1.63 | 1 | 1 | 1 | 1.25 | N/A |
| Polyester | 16 | 3.00 | 3.00 | 1.75 | 2.50 | 1.75 | 1.88 | N/A |
| Dispersion + MQ Resin | 17 | 1.00 | 2.00 | 2.75 | 2.25 | 1.25 | 2.00 | 0.028 |
| Dispersion + MQT Resin | 18 | 1.00 | 2.00 | 2.75 | 2.50 | 1.00 | 2.00 | 0.003 |
| Dispersion + MQ Resin + T-Propyl Resin | 19 | 1.00 | 1.75 | 1.25 | 2.00 | 1.00 | 2.00 | 0.003 |
| Disperison + MQT Resin + MQ Resin + T-Propyl Resin | 20 | 1.38 | 2.00 | 1.00 | 1.25 | 1.00 | 1.75 | 0.003 |
| Dispersion + Polyester | 21 | 3.00 | 3.00 | 3.00 | 2.50 | 1.50 | 1.25 | 0.060 |

The same evaluations performed in Example 1 were also performed in Example 2. The same synergistic performance for olive oil resistance with a cotton pad can be seen for most formulations. Interestingly, the polyester does not exhibit this synergistic behavior. However, when the polyester film former was used (here, Dilinoleic Acid/Butanediol Copolymer), the swelling was measured at 0.06 mm, which is very close to the swelling of the dispersion alone. Further, while there is no observable swelling of the MQT/MQ/T combination (sample 20), the wear with the dispersion is very good. For example, compared to the samples with just the MQ resin (17), the MQT resin (18), and the MQ resin with the T-propyl resin (19) samples, sample 20 had unexpectedly better saliva resistance, which is critical for a lip product. Separately, the MQ/T combinations have good wear performance and could allow for release of water-soluble actives while maintaining the wear resistance.

Those skilled in the art will recognize or be able to ascertain using no more than routine experimentation, many equivalents to the specific embodiments of the invention described herein. Such equivalents are intended to be encompassed by the following claims.

What is claimed is:

1. A cosmetic composition for use on lips, comprising:
   A. a Pickering dispersion of a hydrogel in oil, comprising:
      (i) ethylenic polymeric core particles forming the hydrogel, each ethylenic polymeric core particle obtained by polymerization of monomers of:
         (a) ($C_1$-$C_4$) alkyl ($C_1$-$C_4$) (alkyl) acrylate in which the ($C_1$-$C_4$) alkyl group(s) are optionally substituted by one or more hydroxy groups and/or (di) ($C_1$-$C_4$) (alkyl) amino groups;
         (b) poly [oxy ($C_1$-$C_4$) alkylene] ($C_1$-$C_4$) (alkyl) acrylate; and/or
         (c) ethylenic monomers comprising one or more groups selected from carboxy, anhydride, phosphoric acid, and sulfonic acid;
      (ii) a polymeric stabilizing agent chosen from:
         (d) ethylenic polymers of ($C_1$-$C_6$) (alkyl) acrylate of ($C_3$-$C_{12}$) cycloalkyl monomers; and/or
         (e) copolymers of ethylenic monomers of ($C_1$-$C_6$) ($C_3$-$C_{12}$) cycloalkyl (alkyl) acrylate and ($C_1$-$C_4$) alkyl ($C_1$-$C_4$) (alkyl) acrylate; and
      (iii) a fatty substance that is liquid at 20° C. and 1 atmosphere;
   B. a transfer-resistant film former.

2. The cosmetic composition according to claim 1, wherein the transfer-resistant film former includes a silicone pullulan, a silicone norbornene, a pseudo block copolymer, a MQ resin, a T propyl siloxane resin, a MQT resin, or a combination thereof.

3. The cosmetic composition according to claim 1, wherein the transfer-resistant film former is a MQ resin, a polyester, a trimethylsiloxymethacrylate copolymer, and a dimethicone copolymer.

4. The cosmetic composition according to claim 1, wherein the dispersion further comprises an additional particle, the additional particle having a different chemical structure from the ethylenic polymeric core particle, the additional particle obtained by polymerization of monomers chosen from ethylenic monomers of (a), (b), and/or (c).

5. The cosmetic composition according to claim 1, wherein the ethylenic polymers of ($C_1$-$C_6$) (alkyl) acrylate of ($C_3$-$C_{12}$) cycloalkyl monomers are ethylenic homopolymers of ($C_1$-$C_6$) (alkyl) acrylate of ($C_3$-$C_{12}$) cycloalkyl.

6. The cosmetic composition according to claim 3, wherein the ethylenic polymers of ($C_1$-$C_6$) (alkyl) acrylate of ($C_3$-$C_{12}$) cycloalkyl monomers are ethylenic homopolymers of ($C_3$-$C_{12}$) cycloalkyl (meth) acrylate.

7. The cosmetic composition according to claim 1, wherein the copolymers of ethylenic monomers of ($C_1$-$C_6$) ($C_3$-$C_{12}$) cycloalkyl (alkyl) acrylate and ($C_1$-$C_4$) alkyl ($C_1$-$C_4$) (alkyl) acrylate are copolymers of ($C_3$-$C_{12}$) cycloalkyl (meth) acrylate and (C1-C4) alkyl (meth) acrylate.

8. The cosmetic composition according to claim 1, wherein the fatty substance is a volatile hydrocarbon.

9. The cosmetic composition according to claim 1, further comprising a hydrophilic active agent.

10. The cosmetic composition according to claim 9, wherein the hydrophilic active agent is a moisturizing agent, a desquamating agent, a humectant, an anti-aging agent, a healing agent, an antibacterial agent, a texture modifier, a colorant, a pigment modifying agent, a skin lightening agent, a vitamin, a swelling agent, or a combination thereof.

11. The cosmetic composition according to claim 1, further comprising water, a colorant, an antioxidant, an ultraviolet (UV) filter, a mattifying agent, or a combination thereof.

12. A cosmetic composition for use on lips, comprising:
A. a Pickering dispersion of a hydrogel in oil, comprising:
 (i) ethylenic polymeric core particles forming the hydrogel, each ethylenic polymeric core particle obtained by polymerization of monomers of:
  (a) ($C_1$-$C_4$) alkyl ($C_1$-$C_4$) (alkyl) acrylate in which the ($C_1$-$C_4$) alkyl group(s) are optionally substituted by one or more hydroxy groups and/or (di) ($C_1$-$C_4$) (alkyl) amino groups;
  (b) poly [oxy ($C_1$-$C_4$) alkylene] ($C_1$-$C_4$) (alkyl) acrylate; and/or
  (c) ethylenic monomers comprising one or more groups selected from carboxy, anhydride, phosphoric acid, and sulfonic acid;
 (ii) a polymeric stabilizing agent chosen from:
  (d) ethylenic polymers of ($C_1$-$C_6$) (alkyl) acrylate of ($C_3$-$C_{12}$) cycloalkyl monomers; and/or
  (e) copolymers of ethylenic monomers of ($C_1$-$C_6$) ($C_3$-$C_{12}$) cycloalkyl (alkyl) acrylate and ($C_1$-$C_4$) alkyl ($C_1$-$C_4$) (alkyl) acrylate;
 (iii) a fatty substance that is liquid at 20° C. and 1 atmosphere; and
B. a hydrophilic active agent incorporated into ethylenic polymeric core particle.

13. The cosmetic composition according to claim 12, wherein the dispersion further comprises an additional particle, the additional particle having a different chemical structure from the ethylenic polymeric core particle, the additional particle obtained by polymerization of monomers chosen from ethylenic monomers of (a), (b), and/or (c).

14. The cosmetic composition according to claim 12, wherein the ethylenic polymers of ($C_1$-$C_6$) (alkyl) acrylate of ($C_3$-$C_{12}$) cycloalkyl monomers are ethylenic homopolymers of ($C_1$-$C_6$) (alkyl) acrylate of ($C_3$-$C_{12}$) cycloalkyl.

15. The cosmetic composition according to claim 14, wherein the ethylenic polymers of ($C_1$-$C_6$) (alkyl) acrylate of ($C_3$-$C_{12}$) cycloalkyl monomers are ethylenic homopolymers of ($C_3$-$C_{12}$) cycloalkyl (meth) acrylate.

16. The cosmetic composition according to claim 12, wherein the copolymers of ethylenic monomers of ($C_1$-$C_6$) ($C_3$-$C_{12}$) cycloalkyl (alkyl) acrylate and ($C_1$-$C_4$) alkyl ($C_1$-$C_4$) (alkyl) acrylate are copolymers of ($C_3$-$C_{12}$) cycloalkyl (meth) acrylate and (C1-C4) alkyl (meth) acrylate.

17. The cosmetic composition according to claim 12, wherein the fatty substance is a volatile hydrocarbon.

18. The cosmetic composition according to claim 12, wherein the hydrophilic active agent is a moisturizing agent, a desquamating agent, a humectant, an anti-aging agent, a healing agent, an antibacterial agent, a texture modifier, a colorant, a pigment modifying agent, a skin lightening agent, a vitamin, a swelling agent, or a combination thereof.

19. The cosmetic composition according to claim 12, further comprising water, a colorant, an antioxidant, an ultraviolet (UV) filter, a mattifying agent, or a combination thereof.

* * * * *